United States Patent
Smadja et al.

(10) Patent No.: US 11,679,179 B2
(45) Date of Patent: Jun. 20, 2023

(54) DETECTION OF BIOPROSTHETIC VALVE DEGENERATION

(71) Applicants: UNIVERSITE PARIS DESCARTES, Paris (FR); ASSISTANCE PUBLIQUE-HOPITAUX DE PARIS, Paris (FR); INSTITUT NATIONAL DE LA SANTE ET DE LA RECHERCHE MEDICALE, Paris (FR)

(72) Inventors: David Smadja, Paris (FR); Nicolas Gendron, Paris (FR); Richard Chocron, Paris (FR)

(73) Assignees: UNIVERSITE PARIS DESCARTES, Paris (FR); ASSISTANCE PUBLIQUE-HOPITAUX DE PARIS, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 729 days.

(21) Appl. No.: 16/675,806

(22) Filed: Nov. 6, 2019

(65) Prior Publication Data
US 2020/0147264 A1    May 14, 2020

(30) Foreign Application Priority Data
Nov. 9, 2018  (EP) .................................... 18205549

(51) Int. Cl.
*A61F 2/24* (2006.01)
*A61L 27/34* (2006.01)
(Continued)

(52) U.S. Cl.
CPC ............ *A61L 27/34* (2013.01); *A61F 2/2412* (2013.01); *A61L 27/367* (2013.01);
(Continued)

(58) Field of Classification Search
CPC .... A61L 27/34; A61L 27/3625; A61L 27/367; A61L 27/507; A61L 27/54;
(Continued)

(56) References Cited

U.S. PATENT DOCUMENTS

| 4,946,778 A | 8/1990 | Ladner et al. |
| 7,169,573 B2 * | 1/2007 | Kurosawa .......... G01N 33/6893 435/7.1 |

(Continued)

OTHER PUBLICATIONS

Chikwe, et al. "Prosthetic valve selection for middle-aged patients with aortic stenosis." Nat Rev Cardiol. 2010; 7:711-719.
(Continued)

*Primary Examiner* — Suzette J Gherbi
(74) *Attorney, Agent, or Firm* — Pearne & Gordon LLP

(57) ABSTRACT

The invention relates to a method for predicting or diagnosing a risk of bioprosthetic valve degeneration. Further, the invention relates to a medical device, in particular a bioprosthetic valve coated with EPCR less prone to degeneration and/or calcification once implanted.

Figure 1C:
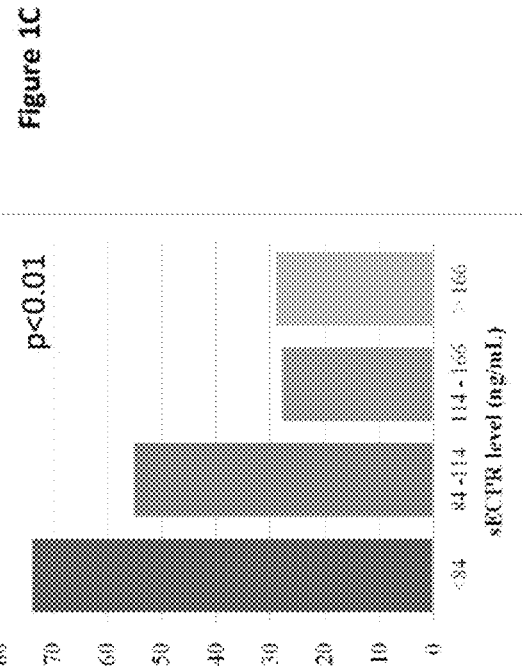

20 Claims, 8 Drawing Sheets
(1 of 8 Drawing Sheet(s) Filed in Color)
Specification includes a Sequence Listing.

(51) Int. Cl.
  A61L 27/36 (2006.01)
  A61L 27/54 (2006.01)
  G01N 33/68 (2006.01)
  A61L 27/50 (2006.01)
(52) U.S. Cl.
  CPC ......... *A61L 27/3625* (2013.01); *A61L 27/507* (2013.01); *A61L 27/54* (2013.01); *G01N 33/68* (2013.01); *G01N 33/6893* (2013.01); *A61L 2300/252* (2013.01); *A61L 2430/20* (2013.01); *G01N 2333/70596* (2013.01); *G01N 2800/32* (2013.01); *G01N 2800/50* (2013.01)
(58) Field of Classification Search
  CPC ........... A61L 2300/252; A61L 2430/20; A61L 2400/02; A61F 2/2412; G01N 33/68; G01N 33/6893; G01N 2333/70596; G01N 2800/32; G01N 2800/50; G01N 2800/323
  See application file for complete search history.

(56) References Cited

U.S. PATENT DOCUMENTS

| | | | | |
|---|---|---|---|---|
| 2006/0286614 | A1* | 12/2006 | Kurosawa | G01N 33/86 435/7.92 |
| 2008/0050832 | A1* | 2/2008 | Buechler | G01N 33/6893 422/68.1 |
| 2014/0322207 | A1* | 10/2014 | Johansson | A61P 17/02 424/133.1 |
| 2020/0147264 | A1* | 5/2020 | Smadja | G01N 33/6893 |

OTHER PUBLICATIONS

Goldstone, et al. "Mechanical or Biologic Prostheses for Aortic-Valve and Mitral-Valve Replacement." New England Journal of Medicine. 2017;377:1847-1857.
Rodriguez-Gabella, et al. "Aortic Bioprosthetic Valve Durability: Incidence, Mechanisms, Predictors, and Management of Surgical and Transcatheter Valve Degeneration." J Am Coll Cardiol. 2017;70:1013-1028.
Skowasch, et al. "Cells of primarily extra-valvular origin in degenerative aortic valves and bioprostheses." European Heart Journal. 2005;26:2576-2580.
Smadja, et al. "Bioprosthetic Total Artificial Heart Induces a Profile of Acquired Hemocompatibility With Membranes Recellularization." J Am Coll Cardiol. 2017;70:404-406.
Pibarot, et al. "Prosthetic Heart Valves: Selection of the Optimal Prosthesis and Long-Term Management." Circulation. 2009;119:1034-1048.
Rutkovskiy, et al. "Valve Interstitial Cells: The Key to Understanding the Pathophysiology of Heart Valve Calcification." J Am Heart Assoc. 2017;6 (23 pages).
Smadja, et al. "Standardization of methods to quantify and culture endothelial colony-forming cells derived from peripheral blood: Position paper from the International Society on Thrombosis and Haemostasis SSC." J Thromb Haemost. Jul. 2019;17(7):1190-4.
Pan, et al. "Mass spectrometry based targeted protein quantification: methods and applications." J Proteome Res. Feb. 2009; 8(2): 787-797.
Jordan, et al. "Bioengineered self-seeding heart valves." J Thorac Cardiovasc Surg. Jan. 2012;143(1):201-8.
Dong X, et al. (2009). "RGD-modified acellular bovine pericardium as a bioprosthetic scaffold for tissue engineering." J Mater Sci Mater Med, vol. 20, pp. (2327-2336).
Smadja, et al. "Interleukin 8 is differently expressed and modulated by PAR-1 activation in early and late endothelial progenitor cells." J Cell Mol Med. Aug. 2009; 13(8b): 2534-2546.
Smadja, et al. "Increased VEGFR2 expression during human late endothelial progenitor cells expansion enhances in vitro angiogenesis with up-regulation of integrin alpha(6)." J Cell Mol Med 2007; 11: 1149-61.
Saposnik, et al. "Alternative mRNA is favored by the A3 haplotype of the EPCR gene PROCR and generates a novel soluble form of EPCR in plasma." Blood. 2008;111(7):3442-3451. doi:10.1182/blood-2007-08-104968.
Zhou, et al. "Promotion of adhesion and proliferation of endothelial progenitor cells on decellularized valves by covalent incorporation of RGD peptide and VEGF." J Mater Sci: Mater Med (2016) 27:142 (13 pages).
Yeghiazaryan, et al. "Degenerative valve disease and bioprostheses: risk assessment, predictive diagnosis, personalised treatments." EPMA Journal (2011) 2:91-105.
European search report issued in priority application EP 18205549.1 dated Aug. 5, 2019 (11 pages).

* cited by examiner

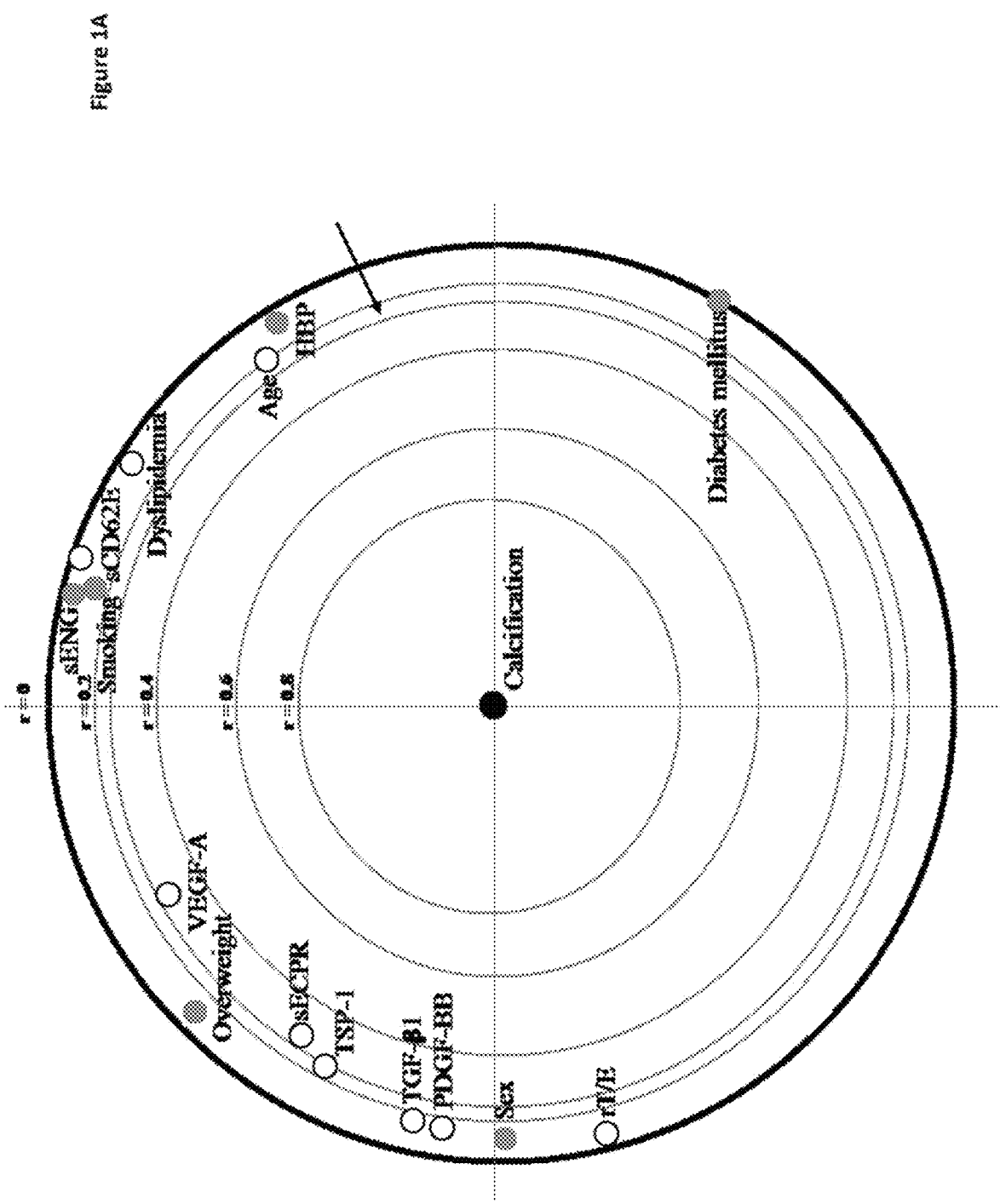

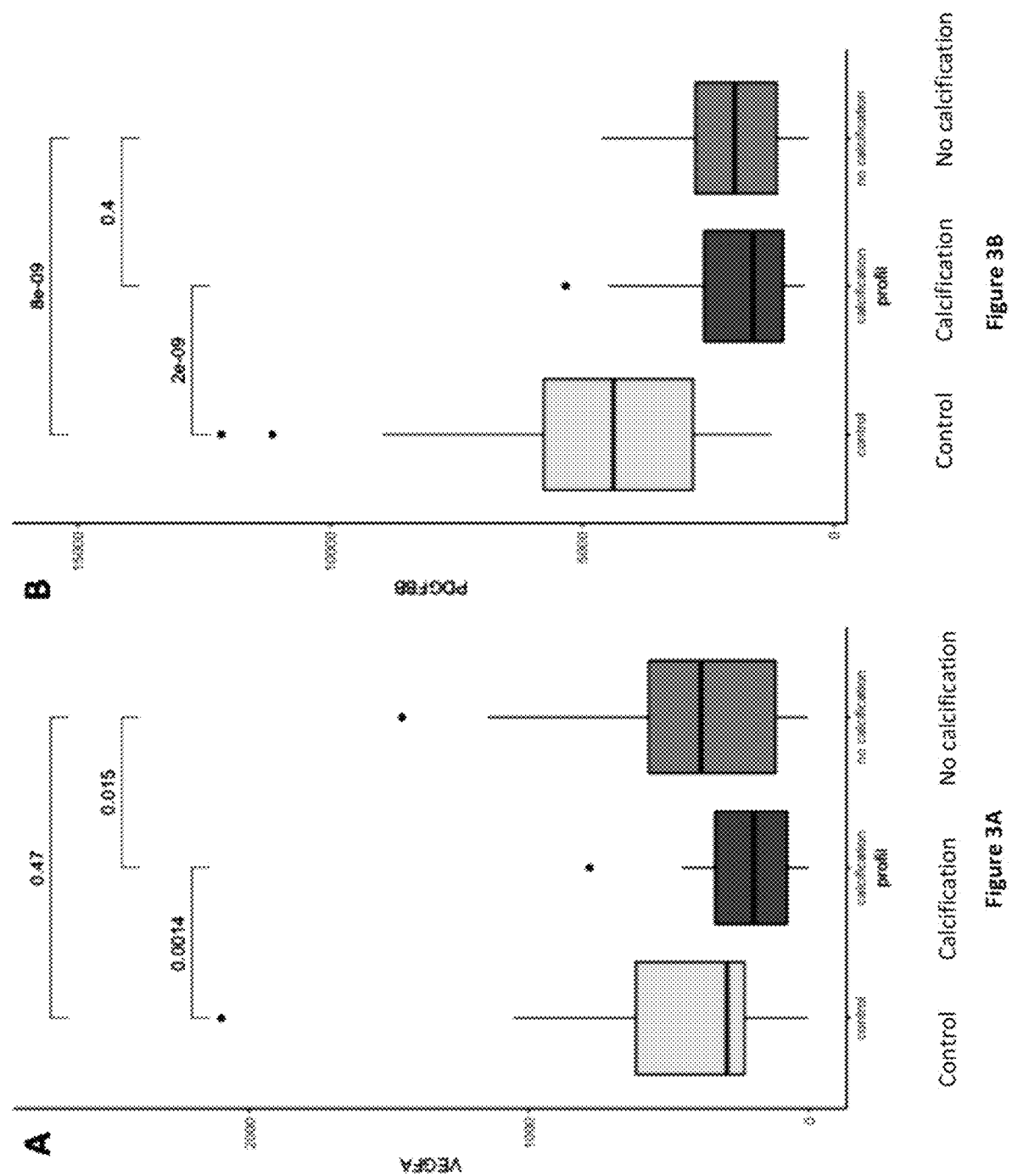

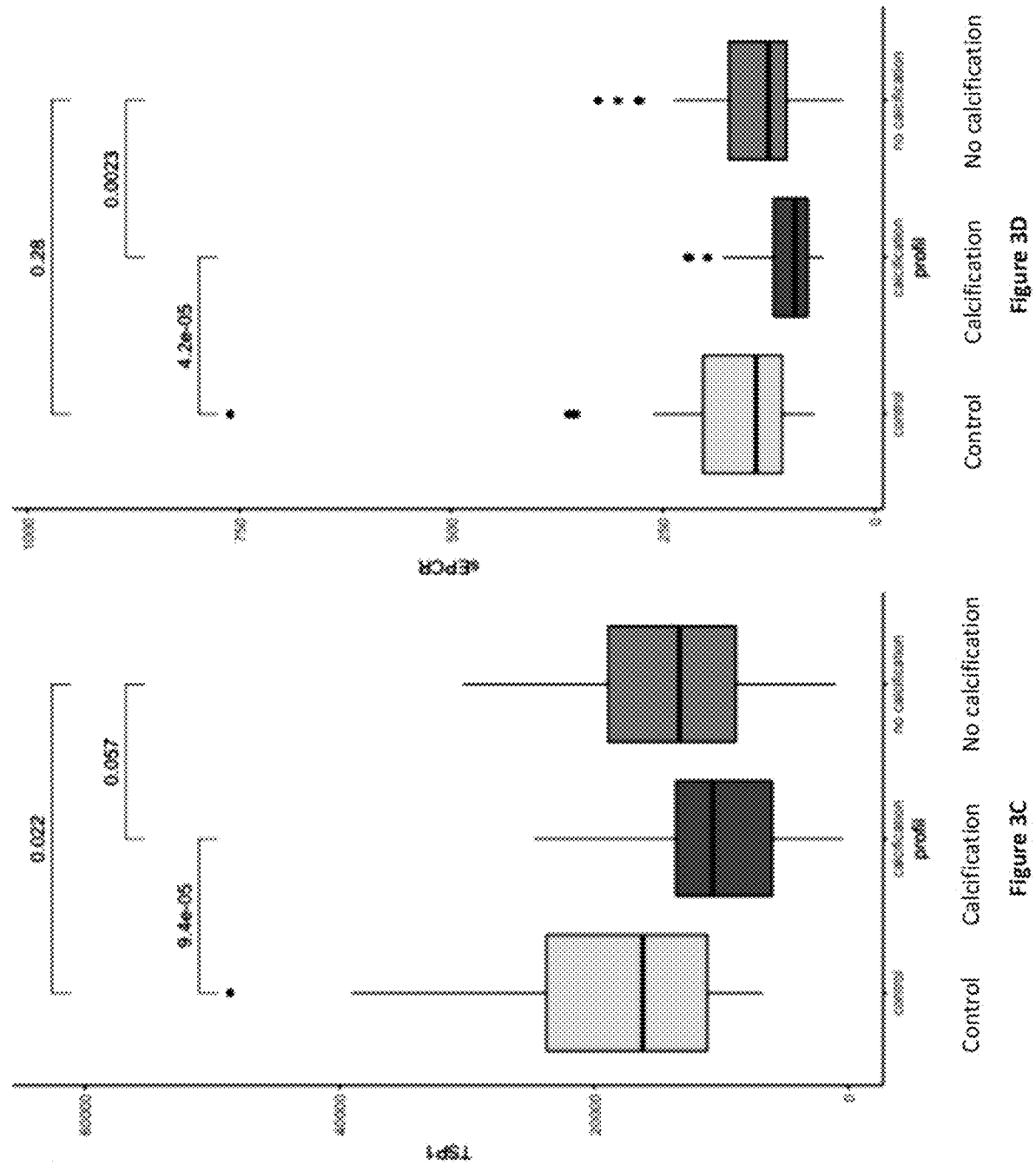

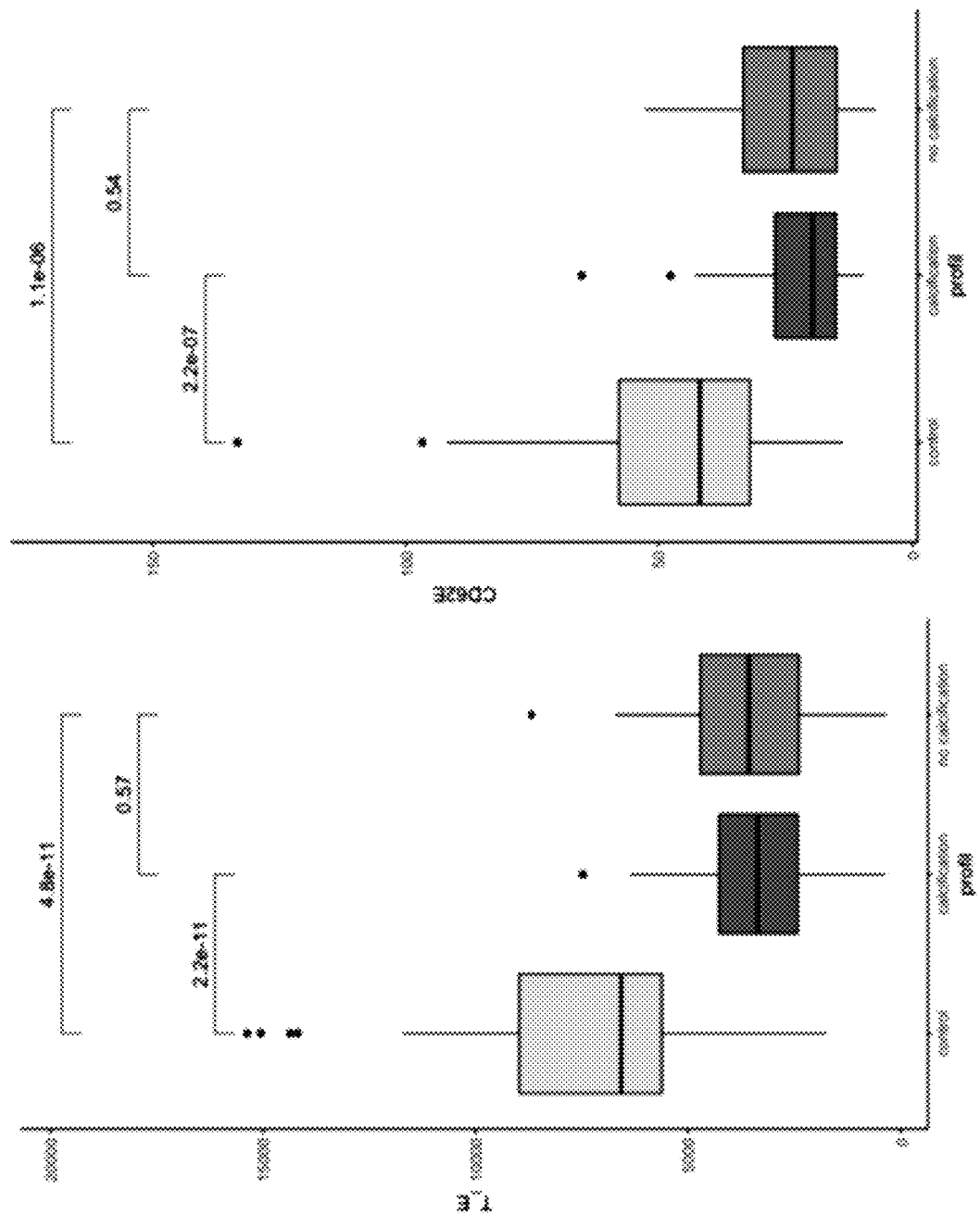

DETECTION OF BIOPROSTHETIC VALVE DEGENERATION

FILED OF THE INVENTION

The present invention relates to the field of medical device, especially to the field of bioprosthetic valve. The inventors identified level or amount of soluble protein for predicting or diagnosing a risk of bioprosthetic valve calcification or degeneration. Further, the invention relates to a medical device, in particular a bioprosthetic valve and a method for producing said bioprosthetic valve comprising a step of coating EPCR over said bioprosthetic valve. The present invention is particularly suited to the identification of bioprosthetic valve degeneration and replacement of said bioprosthetic valve with another one according to the invention.

BACKGROUND OF THE INVENTION

More than 250,000 patients worldwide undergo aortic valve replacement annually, of whom ⅕ are aged between 40-60 years (Chikwe J et al. 2010). Bioprosthetic valves, which do not need long-term anticoagulant treatment, are currently preferred to mechanical valves (Goldstone A B et al. 2017). The main disadvantage of bioprosthetic valves is their limited durability due to structural valve degeneration (SVD), an issue in young patients (Rodriguez-Gabella T et al. 2017). Acquired hemocompatibility, allowing no need for long term anticoagulation medication, is attributed to the deposition of protein strands, blood cells and endothelial cells (EC) on top of bioprosthetic materials. Even only scarce data are available for bioprosthetic valves concerning the cellularization of textured biomaterial surfaces (Shetty R et al. 2006; Noble S et al. 2009), but data on glutaraldehyde-treated bioprosthetic valves are informative. Indeed, initially acellular, these valves when further explanted were shown to be colonized by endothelial progenitors, αSMA expressing cells, macrophages and dendritic cells associated with secretion of an extracellular matrix (Shetty R et al. 2006; Skowasch D et al. 2005). It was suggested that EC present on valve surface derive from vasculogenic progenitor cells mobilized from bone marrow (Smadja D M et al. 2017).

SVD is mostly due to calcification of the bioprosthetic tissue and has been related to immune mechanisms and inflammation consecutive to the allografts (Pibarot P et al. 2009). In native aortic valve stenosis, calcification is also attributed to valvular interstitial cells differentiation in osteoblast-like cells (Rutkovskiy A et al. 2017). αSMA expressing cells are found in degenerative bioprosthetic valves and could result from migration of progenitor cells through disruptive EC on top of bioprosthetic tissue (Skowasch D et al. 2006). Disruption of bioprosthetic valve endothelial recovery after implantation, which initially allows hemocompatibility and non-thrombogenicity, could lead to long-term recruitment and proliferation of fibroblastic and/or pro-calcific cells.

Thus, there is a need for increasing the durability of bioprosthetic valve and decreasing or inhibiting structural valve degeneration (SVD) in particular when considering bioprosthetic valve replacement in young patients. Thus, it seems challenging to propose monitoring bioprosthetic valve degeneration, in particular calcification, to improve the durability of bioprosthetic valve and limiting the numbers of bioprosthetic valve replacement.

SUMMARY OF THE INVENTION

The invention is particularly suited for identifying a calcification process of a bioprosthetic valve and treating patient in need thereof with a bioprosthetic valve according to the present invention. Indeed the inventors surprisingly found that levels or amount of soluble endothelial protein C receptor (sEPCR) is particularly suited for identifying, detecting, diagnosing, predicting a risk of bioprosthetic valves degeneration, especially calcification process.

Accordingly, the invention relates to a method for diagnosing or monitoring a risk of bioprosthetic valve degeneration in a subject, said method comprising the following steps:

i) measuring sEPCR level or amount in a biological sample previously collected from said subject, and ii) comparing said level or amount to a reference, wherein diagnostic or monitoring is based on the result of the comparing step.

In particular embodiments of said method:

measuring sEPCR level or amount according to step i) comprises contacting said sample with a sEPCR binding partner, it further comprises a pretreatment step of the biological sample before step i), it comprises a transformation of sEPCR for measuring the level or amount of sEPCR, and, optionally step i) further comprises contacting the transformed sEPCR with a binding partner capable of selectively interacting with said transformed sEPCR, when the level of sEPCR is lower than 130 ng/mL, preferably 110 ng/mL, then the subject is diagnosed as suffering or at risk of suffering from bioprosthetic tissue degeneration more particularly bioprosthetic valve degeneration, even more particularly from valve microcalcification, calcification and calcification and thrombosis, when the level of sEPCR is lower than 108 ng/mL then the subject is diagnosed as suffering or at risk of suffering from bioprosthetic tissue degeneration more particularly bioprosthetic valve degeneration, even more particularly from valve microcalcification, calcification and calcification and thrombosis, the sample is selected from whole blood, serum or plasma, or It further comprises a step iii) consisting in implementing appropriate health care measures for said subject when the sEPCR level or amount is lower than the reference level or amount defined in step ii), said health care measures being optionally selected from administering to said subject at least one anticoagulant medication, at least one preventive treatment or measure of heart failure or atrial fibrillation, performing on said subject an echocardiography, or a combination thereof.

A particular object of this invention is a device adapted for carrying out the method according to the invention of diagnosing or monitoring a risk of bioprosthetic valve degeneration in a subject, said device comprising:

an analyzing unit adapted for measuring the amount or level of sEPCR in a sample of a subject; and an evaluation unit comprising a stored reference and a data processor having implemented an algorithm for comparing the amount of sEPCR measured by the analyzing unit with at least one stored reference.

Furthermore, as shown in experimental section, inventor have notably found that degenerated bioprostheses are characterized by a loss of endothelization and a loss in EPCR expression in the cells having colonized the bioprosthesis, in comparison with healthy bioprosthesis. Also, the inventors have identified that a coating of EPCR is beneficial because it protects bioprosthetic tissue from degeneration and notably calcification.

Hence another object of the invention is a bioprosthetic tissue to be implanted in the body of a subject coated with EPCR protein, sEPCR, extracellular part of EPCR, or a fragment thereof.

In a particular embodiment, the EPCR protein, sEPCR, extracellular part of EPCR, or a fragment thereof is chemically grafted on said bioprosthetic tissue. In another particular embodiment, said tissue is colonized with cells expressing EPCR.

Said tissue can be made of any suitable tissue, in particular of bovine, calf, equine, or porcine pericardium, or of porcine aortic valve.

Another object of this invention is a bioprosthetic valve comprising said bioprosthetic tissue.

Also, the bioprosthetic valves of the invention being less prone to degeneration, a further object of the invention relates to a method of treating valvopathy comprising using a bioprosthetic valve as defined above.

The invention also relates to a method of treating slowing or stopping bioprosthetic valve degeneration and/or calcification in a subject suffering or at risk of suffering from valve degeneration and/or calcification, comprising administering to the subject such as at least one anticoagulant medication, selected from:

a vitamin K antagonist, such as warfarin, acenocoumarol, phenprocoumon, dicoumarol, tioclomarol, tercafarin, ethyl biscoumacetate, fluindione, phenindione, clorindione, diphenadione, chlorophacinone, anisindione, an heparinoid such as LMWH or fondaparinux, an antiplatelets agents, such as acetylsalicylic acid, clopidogrel, ticlopidine, prasugrel, dipyridamole, cilostazol, ticagrelor, cangrelor, elinogrel, a thrombin inhibitor, such as desirudine, lepidurine, argatroban, melagatran, ximelagatran, bivirudine, dabigatran etexilate, an inhibitor of factor Xa, such as rivaroxaban, apixaban, edoxaban, other antiplatelet agents such as defibrotide or dermatan sulfate, or a combination thereof.

LEGEND OF DRAWING

The patent or application file contains at least one drawing executed in color. Copies of this patent or patent application publication with color drawing(s) will be provided by the Office upon request and payment of the necessary fee.

FIG. 1. Soluble EPCR is associated with bioprosthesis calcification. Focused PCA of the calcification of bioprosthetic valve against clinical factors (age, sex, diabetes mellitus, hypertension (HBP), overweight, dyslipidemia, smoking) and different biomarkers (VEGF-A for vascular endothelial growth factor A; PDGF-BB for platelet derived growth factor BB; TSP-1 for thrombospondin-1; sCD62E for soluble E-selectin; sEPCR for soluble endothelial protein C receptor; sENG for soluble endoglin; TGF-β1 for tumor growth factor beta 1; rT/E for ratio TGF-β1/sENG.). Variables inside the circle represented with an arrow on FIG. 1A are significantly correlated to the dependent variables (calcification of bioprosthetic valve) with p<0.05. Grey variables (Diabetes, mellitus, HBP, sENG, Smoking, Overweight and Sex) are positively correlated to the dependent variable and white variables (Age, Dyslipidemia, sCD62E, VEGF-A, sEPCR, TSP-1, TGFβ1, PDGF-BB and rT/E) are negatively correlated. FIG. 1A is a graphical representation. Histograms also are provided showing proportion of calcified bioprostheses (northing) according to the level divided into interquatiles (easting) of: VEGF-A (FIG. 1B); sEPCR (FIG. 1C); TSP-1 (FIG. 1D) and patient's age at the valve implantation (FIG. 1E). In FIGS. 1B-1D, p represents the p for trend.

Figure 2:
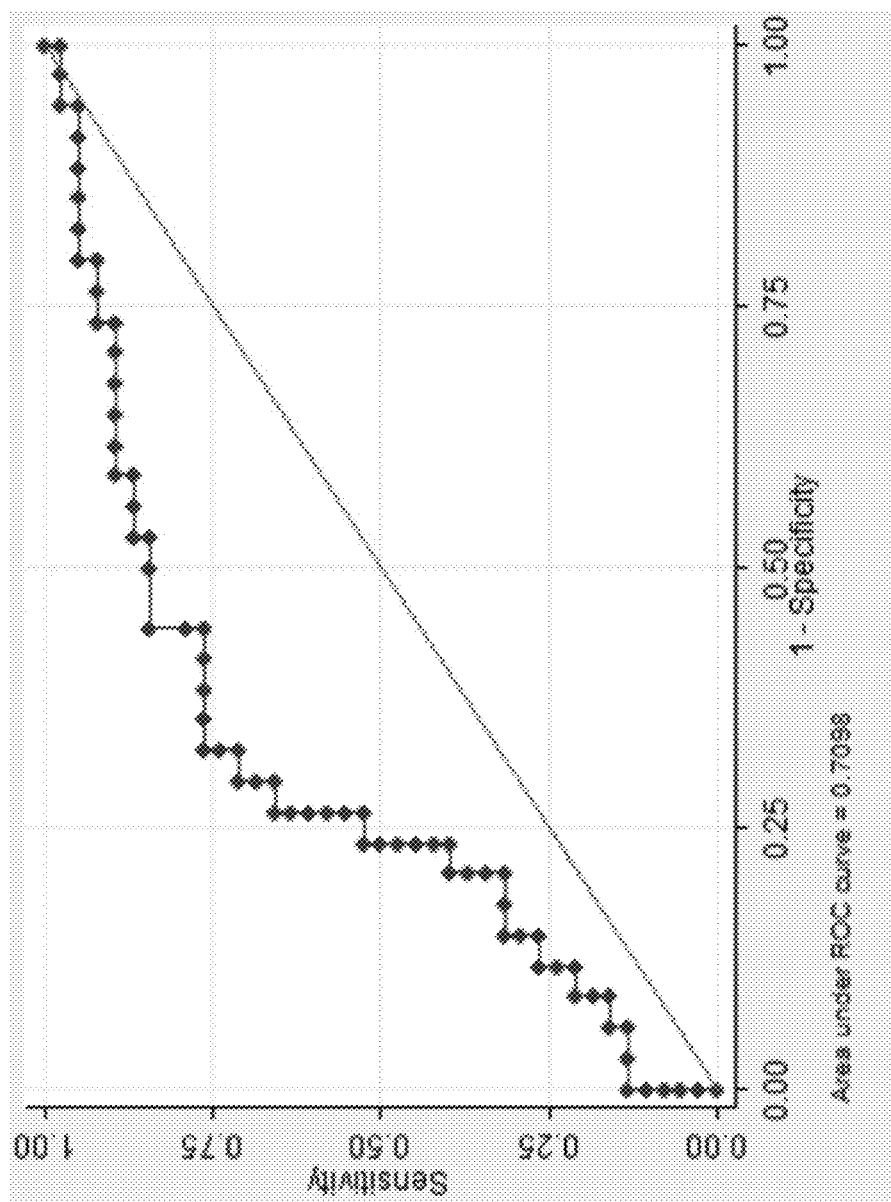

FIG. 2. ROC curve of sEPCR to predict bioprosthetic valve calcification. This graph shows the receiver operating characteristic (ROC) curve of the ability of value of sEPCR for predicting bioprosthetic valve calcification. The area under the ROC curve was 0.709. The optimal threshold for detecting bioprosthetic valve calcification is less than 110.40 ng/mL with 71.05% sensitivity and 70.59% specificity (see table 4).

Figure 3F:
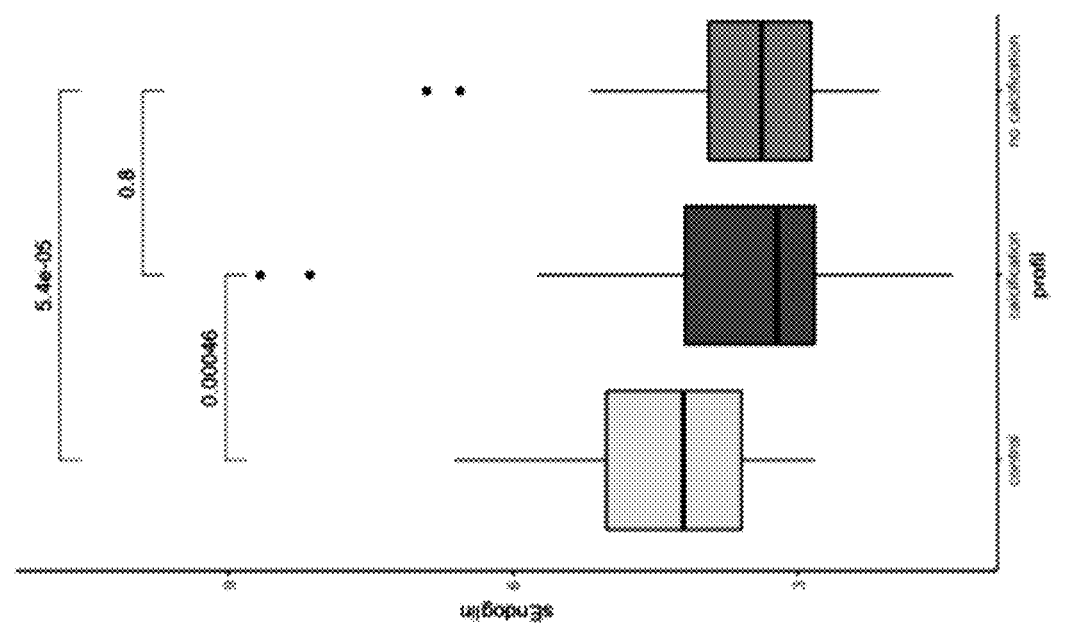
Figure 3E:
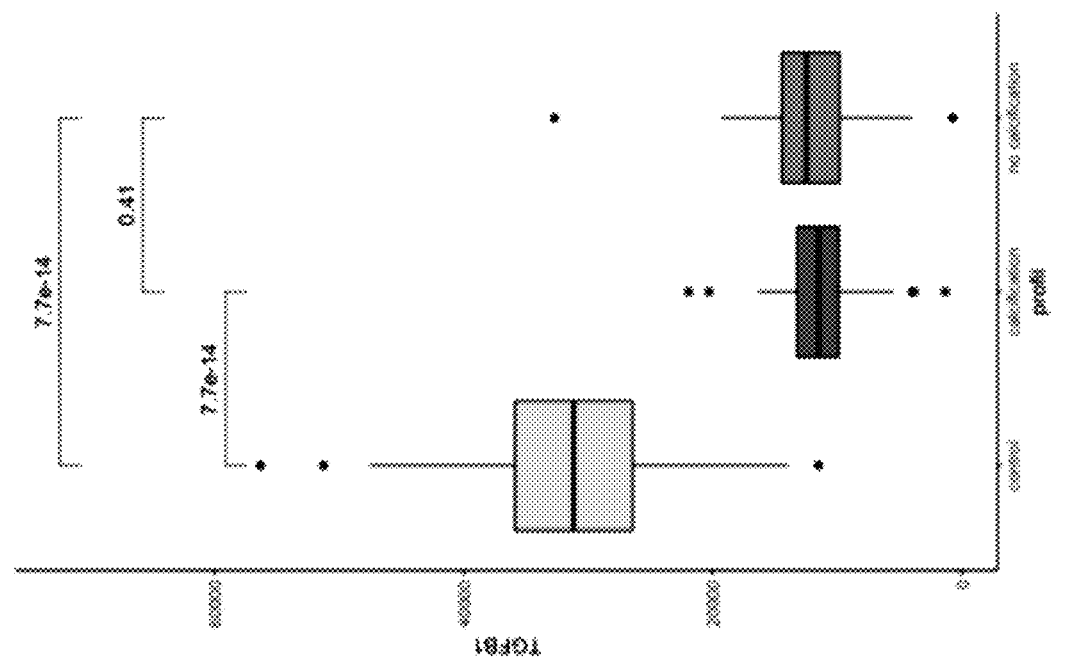

FIG. 3. Boxplots showing levels of VEGF-A (FIG. 3A); PDGF-BB (FIG. 3B); TSP-1 (FIG. 3C); soluble EPCR (FIG. 3D); TGF-β1 FIG. 3E); soluble endoglin FIG. 3F); ratio TGF-β1/soluble endoglin (rT/E) (FIG. 3G); and CD62E FIG. 3H), each according to 3 groups: 1—Controls: Aged- and gender-matched subjects without valve disease from FARIVE study; 2—Calcification: Patients with SVD associated with calcification; 3—No calcification: Patients with SVD without calcification associated.

Figure 4:
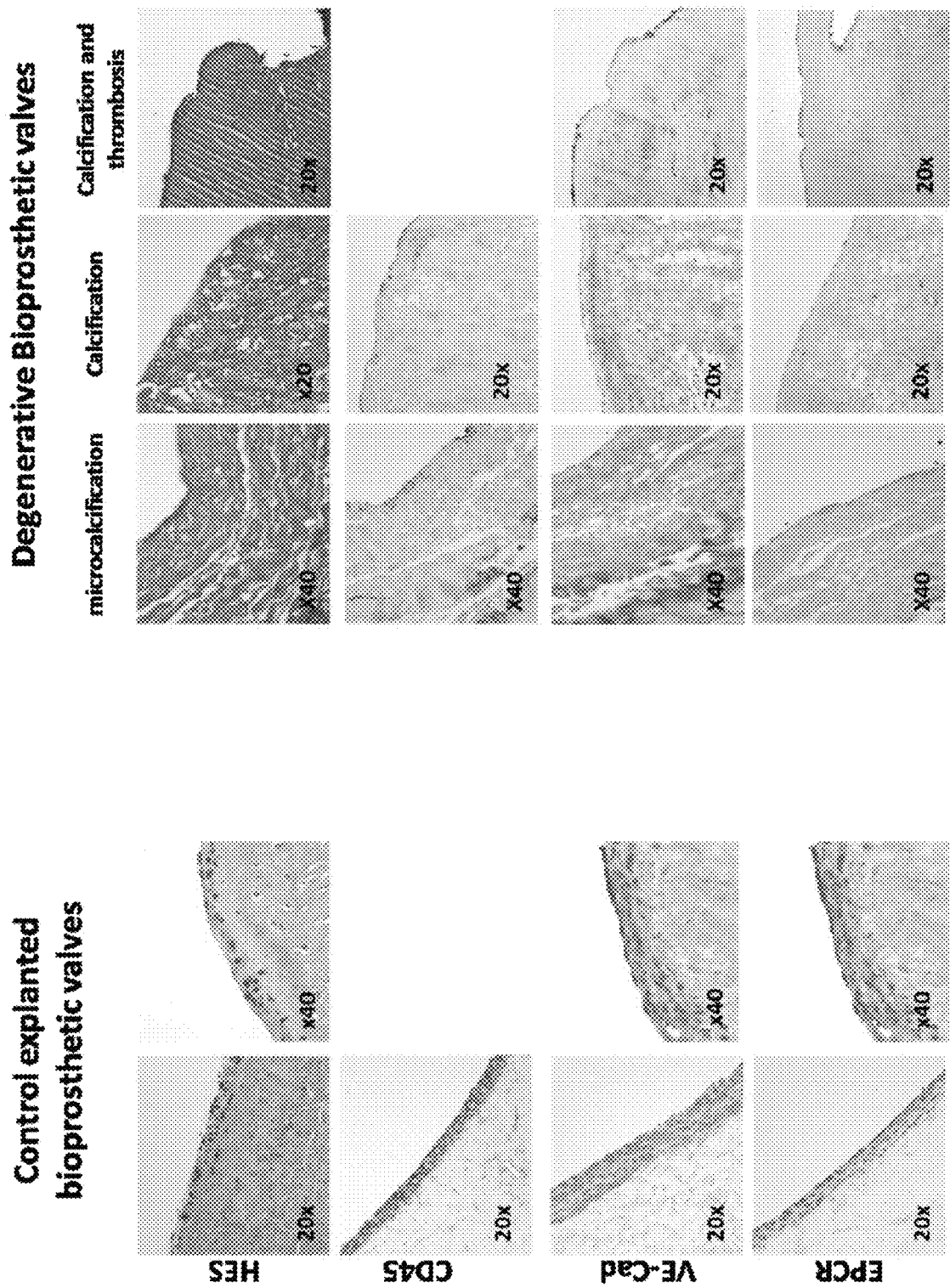

FIG. 4. Immunohistochemistry labelling images of not degenerative and degenerative bioprosthetic valves (microcalcified, calcified and calcified and thrombotic valves). Bioprosthetic valves have been collected from implanted human subjects. Slides have been stained with hematoxylineosin (HES) coloration, and labelled with anti-CD45 (CD45) which labels immunoinflammatory cells, anti-VE cadherin (VE cadherin) which labels endothelial cells or anti-EPCR labels (EPCR) which labels EPCR protein containing structures. VE cadherin label shows that degenerative valves are devoid of endothelial layer in contrast with non-degenerative valves which show a marked outer layer of endothelial cells which express EPCR. Immunoinflammatory cells are found in non-degenerative valves, and also, at a least extend, within microcalcified and calcified valves. Nevertheless, if immune inflammatory cells in non-degenerative valves are labeled with anti EPCR antibodies, no label is detected in degenerative cells.

DETAILED DESCRIPTION OF THE INVENTION

Definitions

As intended herein, the term "comprising" has the meaning of "including" or "containing", which means that when an object "comprises" one or several elements, other elements than those mentioned may also be included in the object. In contrast, when an object is said to "consist of" one or several elements, the object cannot include other elements than those mentioned.

The present invention relates to the identification of a new biomarker of the calcification process of bioprosthetic valves. The inventors surprisingly found that levels or amount of soluble endothelial protein C receptor (sEPCR) is particularly suited for identifying, detecting, diagnosing, predicting a risk of bioprosthetic valves degeneration, especially calcification process.

The term "bioprosthetic valves degeneration" refers to structural valve degeneration (SVD). More particularly, bioprostheses are prone to structural valve degeneration (SVD), resulting in limited long-term durability. SVD usually presents as leaflet calcification resulting in stenosis, but also as leaflet flail or tear resulting in regurgitation. Early SVD is associated with several risk factors; the most common of these risks include young patient age, renal failure, abnormal calcium metabolism, and prosthesis-patient mismatch with the implanted valve. In addition, clinical data suggest that specific types of bioprosthetic valves are more susceptible to early degeneration; many bioprosthetic valves that showed limited durability are no longer used in current clinical practice. A significant challenge when comparing the durability of different types of bioprostheses is the lack of a standardized terminology for the definition of a degenerated prosthetic valve. Previous studies have used and still use different methods and criteria. Therefore, there is a need to have a biomarker for predicting a risk of valve calcification and thus a definition of a degenerated valve.

Therefore, a first aspect of the present invention relates to a method for identifying, predicting or diagnosing a risk of bioprosthetic valve degeneration in a subject, said method comprising determining the level or amount of sEPCR in a biological sample collected from said subject.

Alternatively, the present invention relates to a method for determining or controlling a need for replacement of a bioprosthetic valve of a patient in need thereof, said method comprising determining the level or amount of sEPCR in a biological sample collected from said subject.

Inventors have observed that level of sEPCR is correlated with the risk of bioprosthetic valve calcification. Interestingly, this protein was never found associated with the diagnostic of valve calcification and results of a prospective study provided in the experimental part clearly show that sEPCR level is a good marker for bioprosthetic valve calcification. Therefore, this biomarker is particularly suited for diagnosing, predicting or identifying a bioprosthetic valve calcification and monitoring the need for replacement of said bioprosthetic valve.

The "Soluble endothelial protein C receptor" or "sEPCR" of the invention belongs to the protein C pathway who is a primary regulator of blood coagulation and a critical component of the host response to inflammatory stimuli. The most recent member of this pathway is the endothelial protein C receptor (EPCR), a type I transmembrane protein with homology to CD1d/MHC class I proteins. EPCR, in combination with thrombomodulin, accelerates formation of activated protein C, a potent anticoagulant and anti-inflammatory agent. For example and without reducing the scope of the present invention, the protein that can be used in the present invention is a human EPCR protein (UniProtKB access number Q9UNN8). Alternately, it can be a fragment or any derivative of said protein that conserve the same biological effect or activity. Furthermore it can be a peptide, a polypeptide, a protein or fragment having at least 80% or 85%, or 90%, or 95% identity with the corresponding sequence set forth and accessible under the access number Q9UNN8 (UniProtKB). More particularly said fragment can correspond to the extracellular part of EPCR or to sEPCR. Even more particularly, said fragment or any derivative of EPCR can be glycosylated, especially in order to improve its biological activity, in case where recombinant protein is used in relation with one of the embodiments of the present invention. Glycosylation means of recombinant proteins are well known from those skilled in the art.

As used herein, the term "subject" refers to a mammal, preferably a human. Preferably, it refers to a human patient that is thought to develop or is suspected of suffering from valve calcification or has suffered from valve degeneration in the past and has undergone a valve replacement. Said subject, for example, presents at least one of the following symptoms: chest pain as the heart strains to pump enough blood through the compromised valve, feeling tired after exertion, as when you exercise or move, feeling short of breath, especially after exertion, heart palpitations, or abnormal heartbeats. When said subject have suffered from valve degeneration in the past and have been treated, said patient is therefore monitored for potential valve degeneration recurrence. Said subject may also seem to be healthy but is predisposed to develop a valve degeneration, for example because a member of his family is suffering or has suffered from the same disease.

As used herein the term "biological sample" encompasses a variety of sample types previously obtained from a subject and which can be used in a diagnostic or monitoring assay. Biological samples include but are not limited to whole blood and other liquid samples of biological origin, solid tissue samples such as a biopsy specimen or tissue cultures or cells derived therefrom, and the progeny thereof. For example, biological samples include serum and plasma previously obtained and collected from an individual suspected of having valve degeneration. In a preferred embodiment biological sample is previously obtained from a subject previously treated and monitored for potential valve degeneration recurrence. EPCR exploration on valve explanted during surgery can be done too. In a preferred embodiment of the invention, the sample is whole blood, serum or more preferably plasma.

The term "diagnosing" as used herein means assessing whether a subject as defined above suffers or presents a significant risk of suffering from bioprosthetic tissue degeneration more particularly bioprosthetic valve degeneration, even more particularly from valve microcalcification, calcification and calcification and thrombosis, or not.

According to the present invention, the term "calcification" comprises the conditions selected from microcalcification, calcification and calcification and thrombosis or a combination of those conditions.

The term "monitoring" as used herein means assessing the level or amount of sEPCR over a period of time in a subject as defined above, to determine or to detect a variation in sEPCR level indicating a risk for valve degeneration and/or valve calcification as above defined. In a particular embodiment "monitoring" implies the assessment for sEPCR level or amount in said subject on a regular basis, for example every month, every 2 months, every 3 months, every 4 months, every 5 months, every 6 months or even every year. In another particular embodiment said period of time begins from bioprosthetic valve implantation. In a more particular embodiment said time interval between sEPCR level and/or amount assessments is getting shorter as the time from valve implementation goes by. An example of time interval between two assessments could vary from once a year to twice a year, or three times a year, or four times a year, or five times a year, or six times a year, or seven times a year, or eight times a year, or nine times a year, or ten times a year, or eleven times a year. Another example of time interval between two assessments could vary from twice a year to three times a year, or four times a year, or five times a year, or six times a year, or seven times a year, or eight times a year, or nine times a year, or ten times a year, or eleven times a year.

The term "reference" as used herein means a reference level or amount of sEPCR. This reference can be an absolute value for said level or amount as determined herein. In another embodiment it can be a reference value or status corresponding to a level or amount of sEPCR as measured in a reference sample. In a particular embodiment, the reference value or status corresponding to a level or amount of sEPCR is a mean average calculated from a pool of samples previously obtained from subjects not suffering or not being at risk of suffering from valve degeneration or calcification. Said reference shall allow for differentiating between a subject suffering or at risk of suffering from valve degeneration or calcification and a subject not suffering or not being at risk of suffering from valve degeneration or calcification.

As used herein, the "reference sample" is used to determine a reference value or status of sEPCR and is a biological sample from a subject that does not suffer from valve calcification. Preferably, it is a biological sample of a healthy subject that has no antecedent of nor predisposition to valve calcification. More preferably, it is a biological sample obtained from a healthy subject or a pool of healthy subjects. Determining the level of sEPCR of the invention in said reference sample enables to set a "reference value" (for quantitative measurements) or "reference status" (for qualitative measurements) that are then compared with the actual expression value (amount) or status (level) of the tested subject. It is possible to use, as "reference amount" or "reference level" in the methods of the invention, an average expression amount or level of the same protein which has been measured in several reference samples.

As discussed above, sEPCR has never be found associated with diagnosing valve calcification in the art and is shown herein as a specific marker with an active role in SVD. Indeed, a decrease in sEPCR level or amount is associated to a decreased EPCR expression on bioprosthetic valve as shown in the experimental section. This decrease in EPCR expression could have multiple pathological effects, including prothrombotic, proinflammatory, antiangiogenic effects and loss of cytoprotection and thereby be implicated in the etiology of valve calcification process. From these findings, inventors have been able to develop new diagnostic and monitoring methods for bioprosthetic valve calcification that provide a valuable improvement over the only actual method which is echocardiography. Also, another aspect of the present invention is to provide a new bioprosthetic valve able to reduce, slow or even inhibit calcification process in comparison with bioprosthetic valve of the art.

Diagnostic of Bioprosthetic Valve Degeneration

The inventors have found for the first time that a specific level of sEPCR can be used as a sensitive and specific biomarker of bioprosthetic valve degeneration process, more particularly bioprosthetic valve calcification. Indeed, the inventors have identified that a level of sEPCR lower than 130 ng/mL, preferably 120 ng/mL and more preferably 110 ng/mL and even more preferably lower than 108 ng/mL is correlated to a significant risk of calcification, and results in a test having a good sensitivity and specificity as shown in table 1 below and in the experimental part.

TABLE 1

Cut-off Identification. sEPCR

| Cutpoint | Sensitivity | Specificity | Correctly Classified | LR+ | LR− |
|---|---|---|---|---|---|
| (>=36.943) | 100.00% | 0.00% | 52.78% | 1.0000 | |
| (>=60.055) | 97.37% | 0.00% | 51.39% | 0.9737 | |
| (>=60.939) | 97.37% | 2.94% | 52.78% | 1.0032 | 0.8947 |
| (>=64.452) | 97.37% | 5.88% | 54.17% | 1.0345 | 0.4474 |
| (>=70.516) | 94.74% | 5.88% | 52.78% | 1.0066 | 0.8947 |
| (>=74.789) | 94.74% | 8.82% | 54.17% | 1.0390 | 0.5965 |
| (>=76.026) | 94.74% | 11.76% | 55.56% | 1.0737 | 0.4474 |
| (>=76.487) | 94.74% | 14.71% | 56.94% | 1.1107 | 0.3579 |

TABLE 1-continued

Cut-off Identification. sEPCR

| Cutpoint | Sensitivity | Specificity | Correctly Classified | LR+ | LR− |
|---|---|---|---|---|---|
| (>=76.714) | 94.74% | 17.65% | 58.33% | 1.1504 | 0.2982 |
| (>=77.333) | 94.74% | 20.59% | 59.72% | 1.1930 | 0.2556 |
| (>=78.6665) | 92.11% | 20.59% | 58.33% | 1.1598 | 0.3835 |
| (>=78.773) | 92.11% | 23.53% | 59.72% | 1.2045 | 0.3355 |
| (>=79.021) | 92.11% | 26.47% | 61.11% | 1.2526 | 0.2982 |
| (>=79.456) | 89.47% | 26.47% | 59.72% | 1.2168 | 0.3977 |
| (>=80.702) | 89.47% | 29.41% | 61.11% | 1.2675 | 0.3579 |
| (>=82.378) | 89.47% | 32.35% | 62.50% | 1.3227 | 0.3254 |
| (>=83.213) | 89.47% | 35.29% | 63.89% | 1.3828 | 0.2982 |
| (>=86.542) | 89.47% | 38.24% | 65.28% | 1.4486 | 0.2753 |
| (>=90.673) | 89.47% | 41.18% | 66.67% | 1.5211 | 0.2556 |
| (>=91.495) | 86.84% | 41.18% | 65.28% | 1.4763 | 0.3195 |
| (>=92.92) | 86.84% | 44.12% | 66.67% | 1.5540 | 0.2982 |
| (>=93.578) | 86.84% | 47.06% | 68.06% | 1.6404 | 0.2796 |
| (>=93.88) | 84.21% | 47.06% | 66.67% | 1.5906 | 0.3355 |
| (>=93.956) | 84.21% | 50.00% | 68.06% | 1.6842 | 0.3158 |
| (>=99.658) | 84.21% | 55.88% | 70.83% | 1.9088 | 0.2825 |
| (>=102.128) | 78.95% | 55.88% | 68.06% | 1.7895 | 0.3767 |
| (>=102.318) | 76.32% | 55.88% | 66.67% | 1.7298 | 0.4238 |
| (>=103.341) | 76.32% | 58.82% | 68.06% | 1.8534 | 0.4026 |
| (>=103.433) | 76.32% | 61.76% | 69.44% | 1.9960 | 0.3835 |
| (>=105.378) | 76.32% | 64.71% | 70.83% | 2.1623 | 0.3660 |
| (>=105.384) | 76.32% | 67.65% | 72.22% | 2.3589 | 0.3501 |
| (>=106.034) | 73.68% | 67.65% | 70.83% | 2.2775 | 0.3890 |
| (>=106.115) | 71.05% | 67.65% | 69.44% | 2.1962 | 0.4279 |
| (>=110.407) | 71.05% | 70.59% | 70.83% | 2.4158 | 0.4101 |
| (>=111.204) | 68.42% | 70.59% | 69.44% | 2.3263 | 0.4474 |
| (>=114.901) | 65.79% | 70.59% | 68.06% | 2.2368 | 0.4846 |
| (>=116.335) | 65.79% | 73.53% | 69.44% | 2.4854 | 0.4653 |
| (>=116.338) | 63.16% | 73.53% | 68.06% | 2.3860 | 0.5011 |
| (>=116.586) | 60.53% | 73.53% | 66.67% | 2.2865 | 0.5368 |
| (>=118.072) | 57.89% | 73.53% | 65.28% | 2.1871 | 0.5726 |
| (>=119.529) | 55.26% | 73.53% | 63.89% | 2.0877 | 0.6084 |
| (>=123.594) | 52.63% | 73.53% | 62.50% | 1.9883 | 0.6442 |
| (>=125.034) | 52.63% | 76.47% | 63.89% | 2.2368 | 0.6194 |
| (>=125.988) | 50.00% | 76.47% | 62.50% | 2.1250 | 0.6538 |
| (>=129.866) | 47.37% | 76.47% | 61.11% | 2.0132 | 0.6883 |
| (>=136.327) | 44.74% | 76.47% | 59.72% | 1.9013 | 0.7227 |
| (>=138.036) | 42.11% | 76.47% | 58.33% | 1.7895 | 0.7571 |
| (>=141.86) | 39.47% | 76.47% | 56.94% | 1.6776 | 0.7915 |
| (>=147.328) | 39.47% | 79.41% | 58.33% | 1.9173 | 0.7622 |
| (>=151.837) | 36.84% | 79.41% | 56.94% | 1.7895 | 0.7953 |
| (>=157.68) | 34.21% | 79.41% | 55.56% | 1.6617 | 0.8285 |
| (>=160.719) | 31.58% | 79.41% | 54.17% | 1.5338 | 0.8616 |
| (>=165.284) | 31.58% | 82.35% | 55.56% | 1.7895 | 0.8308 |
| (>=166.837) | 31.58% | 85.29% | 56.94% | 2.1474 | 0.8022 |
| (>=167.462) | 28.95% | 85.29% | 55.56% | 1.9684 | 0.8330 |
| (>=172.961) | 26.32% | 85.29% | 54.17% | 1.7895 | 0.8639 |
| (>=175.1..) | 26.32% | 88.24% | 55.56% | 2.2368 | 0.8351 |
| (>=176.439) | 23.68% | 88.24% | 54.17% | 2.0132 | 0.8649 |
| (>=179.02) | 21.05% | 88.24% | 52.78% | 1.7895 | 0.8947 |
| (>=179.734) | 21.05% | 91.18% | 54.17% | 2.3860 | 0.8659 |
| (>=194.226) | 18.42% | 91.18% | 52.78% | 2.0877 | 0.8947 |
| (>=196.647) | 15.79% | 91.18% | 51.39% | 1.7895 | 0.9236 |
| (>=209.366) | 15.79% | 94.12% | 52.78% | 2.6842 | 0.8947 |
| (>=217.631) | 13.16% | 94.12% | 51.39% | 2.2368 | 0.9227 |
| (>=220.787) | 13.16% | 97.06% | 52.78% | 4.4737 | 0.8947 |
| (>=236.768) | 13.16% | 100.00% | 54.17% | | 0.8684 |
| (>=277.1..) | 10.53% | 100.00% | 52.78% | | 0.8947 |
| (>=279.336) | 7.89% | 100.00% | 51.39% | | 0.9211 |
| (>=303.023) | 5.26% | 100.00% | 50.00% | | 0.9474 |
| (>=326.122) | 2.63% | 100.00% | 48.61% | | 0.9737 |
| (>326.122) | 0.00% | 100.00% | 47.22% | | 1.0 |

The optimal threshold for the detection of bioprosthetic valve calcification was less than 110.40 ng/mL with 71.05% sensitivity and 70.59% specificity.

Accordingly, in a first aspect, invention relates to methods for diagnosing or monitoring a risk of bioprosthetic valve degeneration in a subject, more particularly bioprosthetic valve calcification, comprising the following steps:

i) measuring sEPCR level or amount in a sample previously obtained from said subject and ii) comparing said level or amount to a reference, wherein the diagnostic or monitoring is based on the result of the comparing step.

Typically, a high or a low level of sEPCR is intended by comparison to a reference.

A level or amount above the reference indicates that the subject is not suffering from bioprosthetic valve degeneration or calcification. A level or amount below the reference indicates that the subject suffers or is at risk of suffering from bioprosthetic valve degeneration or calcification.

In a preferred embodiment according to any method of the invention, a lower level or amount of sEPCR in a sample from a subject compared to the reference according to step ii) indicates the occurrence of a bioprosthetic valve degeneration or a risk thereof in said tested subject; and more particularly the occurrence of a bioprosthetic valve calcification in said tested subject. Conversely, according to any method of the invention, a higher level or amount of sEPCR in the sample from a subject compared to the reference according to step ii) indicates the absence of a bioprosthetic valve degeneration or a low risk thereof; and more particularly of a bioprosthetic valve calcification in said tested subject.

Determining the level of sEPCR of the invention in said reference sample enables to set a "reference value" (for quantitative measurements) or a "reference status" (for qualitative measurements) which is then compared with the actual expression value (amount) or status (level) of the tested subject. It is possible to use, as "reference amount" or "reference level" in the methods of the invention, an average expression amount or level of the same protein which has been measured in several reference samples. Said "control reference amount or level" can be a "threshold value" or a "cut-off value". Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity is determined using a Receiver Operating Characteristic (ROC) curve based on experimental data. Preferably, the person skilled in the art may compare the sEPCR levels (obtained according to the methods of the invention) with a defined threshold value. In one embodiment of the present invention, the threshold value is derived from the sEPCR level determined in a blood sample derived from one or more subjects who are suffering from bioprosthetic valve degeneration and/or calcification. In one embodiment of the present invention, the threshold value may also be derived from sEPCR level determined in a blood sample derived from one or more subjects who are suffering from bioprosthetic valve degeneration and/or calcification. Furthermore, retrospective measurement of the sEPCR levels in properly banked historical subject samples may be used in establishing these threshold values as shown in the experimental section.

As described above, reference can then correspond to a predetermined value, such as the values determined in the retrospective study provided herein.

Accordingly, in another preferred embodiment, observing an amount of sEPCR in the sample from the subject lower than 130 ng/mL, preferably lower than 120 ng/mL is regarded as an indicator of, or a risk of, bioprosthetic valve (or bioprosthetic tissue) degeneration, and more particularly of bioprosthetic valve (or bioprosthetic tissue) calcification.

In a more preferred embodiment, observing an amount of sEPCR in the sample from the subject lower of sEPCR lower than 110 ng/mL, preferably lower than 108 ng/mL is regarded as an indicator of, or a risk of, bioprosthetic valve (or bioprosthetic tissue), and more particularly of bioprosthetic valve (or bioprosthetic tissue) calcification.

The methods of present invention are preferably ex vivo or in vitro methods.

In a preferred embodiment, sEPCR level or amount is measured in a biological sample previously obtained from a subject selected from whole blood, serum or plasma, and more preferably serum or plasma.

Said methods can comprise further steps in addition to above steps i) and ii), some of which are disclosed below. For example, such a further step may be selected from:

sample pre-treatment before sEPCR measure, analysis or evaluation of the results obtained by the methods of the invention, or a combination of results obtained by the methods of the invention with results of other medical examinations or assays.

For example, the methods of the invention can be used for confirming or aiding in the diagnostic of valve calcification along with other medical data.

When related to monitoring the bioprosthetic valve degeneration in a subject, said methods would more likely be used in assessing the temporal evolution of sEPCR level or amount regarding the bioprosthetic valve degeneration. For example, sEPCR levels found to decrease consistently over time in a subject may be interpreted as an evolution toward valve degeneration. Also, regular assessment of sEPCR and the early detection of sEPCR threshold below a limit value or reference level or amount as exposed above, allows the early implementation of medical care and treatment before degradation of overall health condition. sEPCR assessment on a regular basis following valve replacement is actually much more convenient compared to echocardiography which necessitates particular medical equipment and medical appointment and which is more often realized only upon detection of symptoms, i.e. once the disease is already developed, that corresponds to an increased risk of heart injury or other organs and a dramatically decreased in life expectancy to only 30% over three years. Another aspect of sEPCR monitoring methods according to the invention is to evaluate the effect of a therapy or a candidate therapy for treating or slowing valve degeneration or calcification in a subject. Accordingly, in an embodiment a method of the invention comprises the following steps:

i') measuring sEPCR level or amount in a first sample from a subject, ii') measuring sEPCR level or amount in a second sample from same subject wherein the first sample is obtained prior to therapy and second sample is obtained during or following therapy and wherein an increase in the level or amount of sEPCR is indicative of a positive effect of said therapy on valve degeneration or calcification.

In a more particular embodiment, several samples are obtained from the subject during therapy and a stabilization of the level or amount in sEPCR level is observed over time thereby signing a stop in valve degeneration or calcification process. In an even more particular embodiment, a slowdown in the decrease of sEPCR level or amount is observed over time, thereby signing a slowdown of valve degeneration or calcification process.

In a particular embodiment, measured level or amount of sEPCR can be used for patient stratification or classification of the level of the degeneration and/or calcification of the bioprosthetic valve (or bioprosthetic tissue) in regard with the stage of degeneration ranging from e.g. "no degeneration", "microcalcification", "calcification" and "calcification and thrombosis".

In a particular embodiment, as mentioned above, biological sample can be pretreated in order to more conveniently or more precisely detect and measure sEPCR, depending on the detection and quantification method that is used, in the goal of enhancing the detection sensitivity in a complex sample. Also, sample preparation can include separation of the proteins: centrifugation based on the protein's molecular weight; electrophoresis based on mass and charge; HPLC based on hydrophobicity; size exclusion chromatography; and solid-phase affinity based on the protein's affinity for the particular solid-phase that is used. Once separated, sEPCR may be identified based on the known "separation profile", e.g. retention time, for that protein and measured using standard techniques such as those explained below. Alternatively, the separated proteins may be detected and measured by, for example, a mass spectrometer. Sample preparation methods for mass spectrometry-based protein quantification methods are for example described in Pan et al. (2010) and are integrated within the present application by reference.

The level of the sEPCR may be determined by using standard electrophoretic and immunodiagnostic techniques, including immunoassays such as competition, direct reaction such as immunohistochemistry, or sandwich type assays. Such assays include but are not limited to: Western blots, agglutination tests, enzyme-labelled and mediated immunoassays, such as ELISAs, biotin/avidin type assays, radioimmunoassays, immunoelectrophoresis, immunoprecipitation, etc. The reactions generally include revealing labels such as fluorescent, chemiluminescent, radioactive, enzymatic labels or dye molecules, or other methods for detecting the formation of a complex between sEPCR and the antibody, antibodies or aptamer reacted therewith.

Accordingly, in a particular embodiment, the methods of the invention comprise contacting the biological sample, e.g. whole blood, serum or plasma, with a sEPCR binding partner. In another particular embodiment, the methods of the invention comprise contacting serum or plasma with a sEPCR binding partner.

As used therein, "sEPCR binding partner" refers to a molecule specifically designed, produced and purified through bioengineering processes to selectively interacting with sEPCR. The binding partner may be generally an antibody that may be either polyclonal or monoclonal. Although antibodies useful in the implementation of the present invention can be polyclonal, monoclonal antibodies are preferred.

Polyclonal antibodies directed against sEPCR can be produced according to known methods by administering the appropriate antigen or epitope to a host animal selected e.g. from example from pig, cow, horse, rabbit, goat, sheep and mice, among others. Various adjuvants known in the art can be used to enhance antibody production.

Monoclonal antibodies directed against sEPCR can be prepared and isolated using any technique that suits for the production of antibody molecules by continuous cell lines in culture. Techniques for production and isolation include but are not limited to the hybridoma technique originally described by Kohler et al. (Koler et al. Nature. 1975; 256(5517):495-7) and the disclosure of Kohler et al. is therefore integrated by reference to the present application; the human B-cell hybridoma technique (Cote et al Proc Natl Acad Sci USA. 1983; 80(7):2026-30) and the disclosure of Cote et al is therefore integrated by reference to the present application; and the EBV-hybridoma technique (Cole et al., 1985, in "Monoclonal Antibodies and Cancer Therapy," Alan R. Liss, Inc. pp. 77-96) and the disclosure of Cole et al. is therefore is integrated by reference to the present application. Alternatively, techniques described for producing a single chain antibodies (see e.g. U.S. Pat. No. 4,946,778) can be adapted to produce anti-sEPCR, single chain antibodies. The disclosure of U.S. Pat. No. 4,946,778 is therefore integrated by reference to the present application.

Antibodies useful in practicing the present invention also include anti-sEPCR including, but not limited to, F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to sEPCR. For example, phage display of antibodies may be used. In such a method, single-chain Fv (scFv) or Fab fragments are expressed on the surface of a suitable bacteriophage, e.g. M13. Briefly, spleen cells of a suitable host, e.g. mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e.g. bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk et al. (1990) Science, 249, 505-510. The disclosure of Tuerk et al. is therefore integrated by reference to the present application. The random sequence library is obtainable by combinatorial chemical synthesis of DNA. In this library, each member is a linear oligomer, eventually chemically modified, of a unique sequence. Possible modifications, uses and/or advantages of this class of molecules have been reviewed in Jayasena 1999. Peptide aptamers consist of conformationally constrained antibody variable regions displayed by a platform protein, such as E. coli Thioredoxin A, that are selected from combinatorial libraries by two hybrid methods (Colas et al. (1996) Nature, 380, 548-50). The disclosure of Colas et al. is therefore integrated by reference to the present application.

The binding partner able to specifically bind sEPCR such as antibodies or aptamers, can be further modified and labelled with a detectable molecule or substance, such as a fluorescent molecule, a radioactive molecule or any others labels known in the art. Labels known in the art generally provide (either directly or indirectly) a signal which will be quantified in order to deduce the level or amount of sEPCR.

As used herein, the term "labelled", with regard to the binding partner, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example, radioactive molecules include but are not limited to radioactive atom for scintigraphy studies such as I123, I124, In111, Re186, Re188.

The aforementioned assays generally involve the binding of the binding partner (i.e. antibody or aptamer) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. More particularly, an ELISA method can be used, wherein the wells of a microtiter plate are coated with a set of antibodies against sEPCR. A body fluid sample containing or suspected of containing sEPCR is then added to the coated wells. After a sufficient period of incubation to allow the formation of binding partner-sEPCR complexes, the plate(s) can be washed to remove unbound material and a labelled secondary binding molecule is added. The secondary binding molecule is allowed to react with any captured sample marker protein, the plate is washed and the presence of the secondary binding molecule is detected using methods well known in the art.

As the binding partner, the secondary binding molecule may be labelled.

Different immunoassays, such as radioimmunoassay or ELISA, are described in the art. For example, a commercially available Elisa kit has been commercialized by STAGO to quantify sEPCR in plasma (Saposnik et al., Blood 2007).

Accordingly, in an embodiment of the present invention, the method for diagnosing or monitoring bioprosthetic valve degeneration in a subject, more particularly bioprosthetic valve calcification, the step for measuring the level of sEPCR comprises the step of contacting the biological sample with a binding partner capable of selectively interacting with sEPCR, resulting in the formation of a complex between binding partner and sEPCR which is itself quantified. Of course, in this embodiment, when the level or amount of sEPCR is measured and compared to the one of a reference sample, the same step of measuring the level of sEPCR is applied to reference sample, in order to obtain comparable data. A further step of calculation can be applied to obtain absolute quantities if required.

In some instance, the pre-treatment step of the sample can comprise a transformation of sEPCR, in the view of facilitating and improving its detection and/or quantification. Examples for such transformation include, but are not limited to, direct radioactive labelling of whole proteins of the sample (iodination of tyrosine residues, reductive alkylation of amino groups (Rice and Means (1971) etc . . . ). Another transformation can be crosslinking of sEPCR from the sample with a recombinant protein known to highly specifically interact with sEPCR. Such recombinant protein could be, for example, recombinant protein C or recombinant activated protein C (APC), recombinant factor VIIa, or even recombinant proteins from the P. falciparum erythrocyte membrane protein 1 (PfEMP1) family, for example DC8 PfEMP1 (L V et al., 2014). Then the crosslinked complex is measured in the method for diagnosing or monitoring of the invention.

In another instance, for example in mass spectrometry based quantification method, the sample can be submitted to protein digestion, in order to identify and quantify the target protein (i.e. sEPCR) through its peptide mass fingerprinting. In that case, target protein is digested along with other proteins of the sample. Also, in an embodiment, the step i) according to the invention comprises quantifying sEPCR making use of its peptide mass fingerprinting.

Accordingly in a particular embodiment in a method according to the invention of diagnosing or monitoring in a subject bioprosthetic valve degeneration, more particularly bioprosthetic valve calcification, the step i) comprises the step of transforming sEPCR in the sample and contacting the thereby transformed sEPCR with a binding partner capable of selectively interacting with said transformed sEPCR, resulting in the formation of a complex between binding partner and transformed sEPCR which is itself quantified. In a more particular embodiment said transformed sEPCR is radiolabelled. Of course, in the case where the level of sEPCR is compared to the level of sEPCR in a reference sample, the same step of transforming sEPCR is applied for said reference sample. A further step of calculation can be applied to obtain absolute quantities if required.

As shown in the experimental section, Inventors have found for the first time that sEPCR level constitute a valuable biomarker of valve degeneration and/or calcification. More particularly this biomarker allows identifying and detecting valve degeneration and/or calcification independently of any medical imaging, such as echocardiography which is to date the only mean to make with certainty the diagnostic of valve degeneration and/or calcification. This examination is most often implemented once the first signs of SVD occurs, or, at the very least, if performed on a regular basis, with long period of time intervals (from every 3 to every 4 months). Yet, as reported above, once the first symptoms of the disease appeared, it is actually already well installed, which results in a dramatic drop in life duration expectancy. Hence, measure of sEPCR level or amount as a biomarker of valve degeneration provides an easier, more practical and cheaper alternative to echocardiography, and shall allow to take health care measures at the earliest to the benefit of the subject. These measures can be for example the implementation of preventive treatment to overcome the complications of valvopathies such as heart failure or atrial fibrillation, the implementation of a more rigorous medical survey of cardiovascular functions, the implementation of treatments for valve degeneration and/or calcification, in order to prevent, stop or slow the progression of the condition or disease.

Accordingly another object of this invention lies in a method for diagnosing or monitoring bioprosthetic valve degeneration in a subject, more particularly bioprosthetic valve calcification, comprising the following steps:

i) measuring sEPCR level or amount in a sample from said subject, ii) comparing said level or amount to a reference, wherein diagnostic or monitoring is based on the result of the comparing step i), with potentially any one of the embodiments as exposed before, and further comprising the step iii) consisting of implementing appropriate health care measures for said subject when the sEPCR level or amount is lower than the reference level or amount defined in step ii). Said healthcare measure being administered to the subject a preventive treatment of heart failure and/or atrial fibrillation. Such measures can be for example with symptomatic pharmacological treatment which are known in the art and as well as anticoagulant strategies to prevent thrombotic event. In another particular embodiment, said healthcare measures are performing an echocardiography on the subject.

EPCR is a transmembrane glycoprotein expressed on endothelial cells which is known to bind protein C (PC), to increase the rate of PC activation through thrombin/thrombomodulin complex and to prevent further thrombin formation by inactivating factors Va/VIIIa. Hence, from the discovery by the inventors of the dramatic loss of EPCR on bioprosthetic tissue surface, without wishing to be bound by theory, it can be inferred that it would lead to decreased surface PC activation, and subsequently to increased thrombin generation. Then, thrombin may act by favoring local thrombosis and inflammation in particularly in the allograft context of valve replacement. The decrease in soluble EPCR during SVD could be associated with loss of EPCR-related endothelial coating and loss of EPCR expression resulting in the loss of its natural antithrombotic capacities. Moreover, as shown in the experimental section, fibrin increase calcification which is in favor of a clear link between thrombosis and calcification.

Hence, valve degeneration originating in the loss of EPCR which results in a procoagulant state, anticoagulation medication can be proposed in patients with early phase of degenerative valve to counterbalance said procoagulant state.

Accordingly, in a more particular embodiment said healthcare measure is administering at least one anticoagulant medication such as:

a vitamin K antagonist, such as warfarin, acenocoumarol, phenprocoumon, dicoumarol, tioclomarol, tercafarin, ethyl biscoumacetate, fluindione, phenindione, clorindione, diphenadione, chlorophacinone, anisindione, an antiplatelets agents, such as acetylsalicylic acid, clopidogrel, ticlopidine, prasugrel, dipyridamole, cilostazol, ticagrelor, cangrelor, elinogrel, a thrombin inhibitor, such as desirudine, lepidurine, argatroban, melagatran, ximelagatran, bivirudine, dabigatran etexilate, an inhibitor of factor Xa, such as rivaroxaban, apixaban, edoxaban, other antiplatelet agents such as defibrotide or, dermatan sulfate, an heparinoid such as LMWH or fondaparinux, or a combination thereof.

Also, an object of this invention lies in a method for preventing the complications of valvopathies such as heart failure or atrial fibrillation, comprising the following steps:

i) measuring sEPCR level or amount in a sample from said subject, ii) comparing said level or amount to a reference, wherein diagnostic or monitoring is based on the result of the comparing step, with potentially any one of the embodiments as exposed before, and further comprising the step iii) of, when the subject is diagnosed from the previous step ii) as suffering or at risk of suffering from bioprosthetic valve degeneration and/or calcification, then administering to the subject a preventive treatment or measure for heart failure and/or atrial fibrillation. Such measures can be for example with symptomatic pharmacological treatment which are known in the art and as well as anticoagulant strategies to prevent thrombotic event.

Also, an object of this invention lies in a method for treating, slowing or stopping bioprosthetic valve degeneration and/or calcification, comprising the following steps:

i) measuring sEPCR level or amount in a sample from said subject, ii) comparing said level or amount to a reference, wherein diagnostic or monitoring is based on the result of the comparing step, with potentially any one of the embodiments as exposed before, and further comprising the step iii) of, when the subject is diagnosed from the previous step as suffering or at risk of suffering from valve degeneration and/or calcification, then administering to the subject at least one anticoagulant medication, selected from:

a vitamin K antagonist, such as warfarin, acenocoumarol, phenprocoumon, dicoumarol, tioclomarol, tercafarin, ethyl biscoumacetate, fluindione, phenindione, clorindione, diphenadione, chlorophacinone, anisindione, a heparinoid as LMWH or fondaparinux, an antiplatelets agents, such as acetylsalicylic acid, clopidogrel, ticlopidine, prasugrel, dipyridamole, cilostazol, ticagrelor, cangrelor, elinogrel, a thrombin inhibitor, such as desirudine, lepidurine, argatroban, melagatran, ximelagatran, bivirudine, dabigatran etexilate, an inhibitor of factor Xa, such as rivaroxaban, apixaban, edoxaban, other antiplatelet agents such as defibrotide or, dermatan sulfate, or a combination thereof.

In a particular embodiment, said subject is diagnosed at an early phase of bioprosthetic valve degeneration and/or calcification. In a more particular embodiment, the early phase is characterized by a low level or amount of sEPCR, but no clinical sign of bioprosthetic valve degeneration and/or calcification.

In another embodiment the invention relates to at least one anticoagulant medication for its use in treating, preventing, slowing or stopping bioprosthetic valve degeneration in a subject in need thereof. In a particular embodiment, the invention relates to at least one drug selected from:

a vitamin K antagonist, such as warfarin, acenocoumarol, phenprocoumon, dicoumarol, tioclomarol, tercafarin, ethyl biscoumacetate, fluindione, phenindione, clorindione, diphenadione, chlorophacinone, anisindione, a heparinoid such as LMWH or fondaparinux, antiplatelets agents, such as acetylsalicylic acid, clopidogrel, ticlopidine, prasugrel, dipyridamole, cilostazol, ticagrelor, cangrelor, elinogrel, a thrombin inhibitor, such as desirudine, lepidurine, argatroban, melagatran, ximelagatran, bivirudine, dabigatran etexilate, an inhibitor of factor Xa, such as rivaroxaban, apixaban, edoxaban
other antiplatelet agents such as defibrotide or, dermatan sulfate, or
a combination thereof,
for its use in treating, preventing, slowing or stopping bioprosthetic valve degeneration or bioprosthetic tissue degeneration in a subject in need thereof.

In another embodiment the invention relates to a method of treating, preventing, slowing or stopping bioprosthetic valve degeneration or bioprosthetic tissue degeneration in a subject in need thereof. In a particular embodiment, said method comprise administering to said subject at least one drug selected from:
a vitamin K antagonist, such as warfarin, acenocoumarol, phenprocoumon, dicoumarol, tioclomarol, tercafarin, ethyl biscoumacetate, fluindione, phenindione, clorindione, diphenadione, chlorophacinone, anisindione,
a heparinoid such as LMWH or fondaparinux,
antiplatelets agents, such as acetylsalicylic acid, clopidogrel, ticlopidine, prasugrel, dipyridamole, cilostazol, ticagrelor, cangrelor, elinogrel,
a thrombin inhibitor, such as desirudine, lepidurine, argatroban, melagatran, ximelagatran, bivirudine, dabigatran etexilate,
an inhibitor of factor Xa, such as rivaroxaban, apixaban, edoxaban
other antiplatelet agents such as defibrotide or, dermatan sulfate, or
a combination thereof.

In a particular embodiment, said subject is diagnosed at an early phase of degenerative valve. In a more particular embodiment, the early phase is characterized by a low level or amount of sEPCR, but no clinical sign of bioprosthetic valve degeneration and/or calcification.

Diagnostic/Monitoring Kit

The present invention also relates to a kit adapted for carrying out the methods as exposed above. For instance, a kit according to the invention comprises a binding agent which specifically binds sEPCR and optionally instructions for carrying out the said methods for diagnosing or monitoring in a subject bioprosthetic valve degeneration and/or calcification.

The term "kit" as used herein refers to a collection of the aforementioned components, preferably, provided separately or within a single container. The container also comprises instructions for carrying out the method of the present invention. These instructions may be in the form of a manual or may be provided by a computer program code which is capable of carrying out the calculations and comparisons referred to in the methods of the present invention and to establish a diagnosis accordingly when implemented on a computer or a data processing device. The computer program code may be provided on a data storage medium or device such as an optical storage medium or directly on a computer or data processing device. Moreover, the kit may, preferably, comprise standard amounts or samples of sEPCR for calibration purposes.

Diagnostic/Monitoring Device

Moreover, the present invention relates to a device adapted for diagnosing or monitoring in a subject bioprosthetic valve degeneration and/or calcification by carrying out the methods of the present invention. Said device comprises, at least:
a) an analyzing unit being adapted for measuring the amount or level of sEPCR in a sample of a subject;
b) an evaluation unit comprising a stored reference and a data processor having an algorithm implemented for comparing the amount of sEPCR measured by the analyzing unit of a) with at least one stored reference.
Said reference differentiates: a subject suffering from bioprosthetic valve degeneration and/or calcification, a subject being at risk of suffering from bioprosthetic valve degeneration and/or calcification and a subject not suffering from or not being at risk of suffering from bioprosthetic valve degeneration and/or calcification, or for stratifying patient as a function of the stage of valve degeneration (microcalcification, calcification and calcification and thrombosis).

In a particular embodiment said device is adapted for automatically quantitatively measuring sEPCR and comprises any means useful to perform the measure of sEPCR as exposed above in the analyzing unit, the data obtained can be processed by the evaluation unit via a computer program which runs on a computer (i.e. data processor). In another particular embodiment, the data processor executes the comparison of the level or amount of the biomarker with the reference. Whether in a single device or separated, an operative linkage between the units allows data transfer.

As mentioned, said device is adapted for implementing the diagnosing or monitoring methods according to the invention. In a specific example, the analyzing unit for determining sEPCR comprises a binding agent as described above, such as an antibody, a fragment thereof, or an aptamer, which specifically recognizes sEPCR, and a zone for contacting said binding agent with the sample to be tested. The binding agent may be immobilized on the zone for contacting or may be applied to said zone after the sample has been loaded. The analyzing unit shall be, preferably, adapted for quantitatively measuring the amount of complexes of the agent and sEPCR. The evaluation shall be adapted for determining the level or amount of sEPCR and comparing with the at least one stored reference.

Bioprosthetic Valve

As previously discussed, a lower level of sEPCR can be used as a sensitive and specific biomarker of bioprosthetic valve degeneration and/or calcification. Moreover, as shown in the experimental section, degenerated bioprostheses are characterized by a loss of endothelization and a loss in EPCR expression in the cells having colonized the bioprosthesis, in comparison with healthy bioprosthesis, (i.e. not presenting features of microcalcification, calcification or calcification and thrombosis).

Furthermore, the inventors have identified that a coating of EPCR is beneficial because it limits the risk and the extend of degeneration and/or calcification of bioprosthetic valve and thereby improves its durability, and thus decreases the risk of a medical intervention to change the bioprosthesis and the risk for the patient of developing health threatening valve degeneration deleterious effects. Indeed, experimental data show that bioprosthetic valves presenting EPCR at their surface are less prone to calcification or other degeneration processes. As shown in the experimental part, bioprosthetic valves in which EPCR is detected are less prone to degeneration in comparison with no coating with EPCR. This coating could allow resistance to thrombosis and inflammation when pathological shear stress and/or turbulences are applied on the valve.

Hence, an extended durability of a bioprosthetic valve presenting EPCR at its surface is expected.

Typically, bioprosthetic valves generally include a frame (most often in metal) on which 2 or 3 biological valves are inserted, which can be made of any suitable mammalian tissue, e.g. bovine pericardium, calf pericardium, porcine aortic valves, equine or porcine pericardium. More preferably bioprosthetic valves are made of bovine pericardial tissue, for example this kind of valve are used in hybrid membrane of bioprosthetic Carmat total artificial heart (C-TAH). Biological tissues are generally fixed with glutaraldehyde in order to allow the transformation of their structural proteins into a matrix that does not cause an immunological reaction once implanted. Such tissues are thus acellularized or partially decellularized.

Aldehydes bound and/or adsorbed in valve tissue are suspected to be a cause for valve degeneration and calcification. Very recently, a new valve has been approved by the FDA, it contains a tissue called Resilia® which incorporates a capping anticalcification process to block residual aldehyde groups known to bind with calcium. Nevertheless, it is not coated with EPCR, absence of which is found a key factor in valve degeneration, as shown by the inventors.

Accordingly, a second aspect of the present invention relates to a bioprosthetic heart valve characterized in that said bioprosthetic valve is coated with EPCR. Said coating may be performed by either a chemical grafting of EPCR on the tissue of bioprosthetic valve or by colonization of said tissue or valve with cells expressing EPCR.

In a particular embodiment, said tissue is colonized by endothelial cells (in other word, subjected to endothelization). Obviously, said endothelization is performed before implantation of the prosthesis. In particularly preferred embodiment said endothelial cells are characterized in that they express EPCR. In a more particular embodiment said endothelial cells are engineered to overexpress EPCR. In a very particular embodiment said endothelial cells are endothelial progenitor cells originated from the subject to be implanted. Endothelial progenitor cells collection from a mammal is a well known and standardized method (Smadja D M et al 2019). Endothelial progenitor cells ells can also be obtained from Human umbilical cord bloods from the adherent mononuclear cell (MNC) fraction as described by Smadja et al. (2007).

In a more particular embodiment, the invention relates to a bioprosthetic valve characterized in that EPCR protein is coated over the surface of said bioprosthetic valve to inhibit, reduce or slow degeneration and/or calcification process of the valve once implanted in the body of the subject. In a preferred embodiment of the present invention, the EPCR protein coated over the surface of said bioprosthetic valve is a human EPCR protein (UniProtKB access number Q9UNN8).

The whole amino acid sequence of EPCR as published in Fukudome et al. (1994) (SEQ ID NO: 1) is as following:

SEQ ID NO: 1:
MLTTLLPILLLSGWAFCSQDASDGLQRLHMLQISYFRDPYHVWYQGNASL

GGHLTHVLEGPDTNTTIIQLQPLQEPESWARTQSGLQSYLLQFHGLVRLV

HQERTLAFPLTIRCFLGCELPPEGSRAHVFFEVAVNGSSFVSFRPERALW

-continued
QADTQVTSGVVTFTLQQLNAYNRTRYELREFLEDTCVQYVQKHISAENTK

GSQTSRSYTSLVLGVLVGGFIIAGVAVGIFLCTGGRRC.

In a more preferred embodiment bioprosthetic valve of the invention is coated with an extracellular fragment of EPCR or sPECR. In an even more preferred bioprosthetic valve of the invention is coated with a human extracellular fragment of EPCR or sPECR. From Fukudome et al (1994) the skilled in the art will be able to determine easily extracellular part of EPCR (SEQ ID NO: 2), comprising more or less amino acids 17 to 209 of SEQ ID NO: 1 (i.e. without the signal peptide and transmembrane region).

SEQ ID NO: 2:
CSQDASDGLQRLHMLQISYFRDPYHVWYQGNASLGGHLTHVLEGPDTNTT

IIQLQPLQEPESWARTQSGLQSYLLQFHGLVRLVHQERTLAFPLTIRCFL

GCELPPEGSRAHVFFEVAVNGSSFVSFRPERALWQADTQVTSGVVTFTLQ

QLNAYNRTRYELREFLEDTCVQYVQKHISAENTKGSQTSRSY.

In one embodiment, the sEPCR correspond to the recombinant sEPCR as described in Saposnik et al. (2007).

An object of the invention is also a valve tissue comprising anyone of the above features or any combination thereof. Another object of the invention is a method of treating valvopathies comprising using a bioprosthetic valve of the invention, i.e. coated with EPCR as described above.

Method for Producing EPCR Bioprosthetic Coated Valves

A third aspect of the present invention relates to a method for producing a bioprosthetic valve as described above, wherein said method comprising a step of coating EPCR over said bioprosthetic valve.

Said EPCR coating or endothelization (in other words, colonization of the scaffold of the bioprosthesis by endothelial cells) can be performed in vitro before bioprosthesis implantation.

A number of techniques has been proposed to coat molecules over biomaterial of medical device and are well-known in the art or by skilled person. For example, Chollet C et al. (2007) described a graft of RGD peptides onto poly(ethylene terephthalate) (PET) film surfaces with well controlled densities. Also, RDG peptides were immobilized on decellularized valve scaffolds in order to promote cell adhesion (e.g. Filová F et al. 2009). In another example, U.S. Pat. No. 9,289,53 provides a method for grafting and optimising the presentation of adhesion peptides or biological agents when the scaffold is made from collagen and/or contains accessible thiol, amine or carboxyl groups. Another example for coating molecule on bioprosthetic material is the use of N-ethyl-N'-3-(dimethylaminopropyl)carbodiimide, that activates carboxyl groups to conjugate to amino groups, as used by Jordan J E et al. (2012). Therefore, techniques are well-known by the skilled person to perform coating of a protein, more particularly of EPCR over any biomaterial. This coating can be achieved either through covalent links to the bioprosthetic tissue or non-covalent link. Also, EPCR can be coated onto bioprosthetic tissue as embedded in a polymer. More preferably EPCR is grafted onto bioprosthetic tissue through a covalent link.

In a preferred embodiment, the step of coating EPCR on the surface of the bioprosthetic valve comprises coating sEPCR on the surface of the bioprosthetic valve. In another preferred embodiment the step of coating sEPCR on the surface of the bioprosthetic valve is made through a covalent link.

In another embodiment, the step of coating EPCR over said bioprosthetic valve is made through endothelization of said bioprosthetic valve by endothelial cells, e.g. as exposed in the experimental section. In a particular embodiment, said method comprises a further step of testing and selecting suitable endothelial cells for expression of EPCR before the endothelization. This step can be performed by any convenient means of molecular biology (Western, Southern, IHC etc) known by the skilled in the art. More preferably said endothelial cells are from the subject to be treated, even more preferably these cells are endothelial progenitor cells originated from the subject to be implanted. Hence, in a particular embodiment, said method comprises a further step of obtaining endothelial progenitor cells from the subject to be implanted. In an even more embodiment, said endothelial cells to be implemented may have been engineered to overexpress EPCR.

In the method for producing a bioprosthetic valve as described above, the step of coating EPCR over said bioprosthetic valve can be performed either on the bioprosthetic tissue before, it is mounted on the frame of the prosthesis, or once the tissue is mounted on the frame of the prothesis.

Further aspects and advantages of the invention will be disclosed in the following examples, which should be considered illustrative.

Example

I. sEPCR is a Valuable Biomarker of Valve Degeneration and Calcification Material and Methods Study Population The inventors investigated patients who underwent bioprosthetic surgical valve replacement (SVR) for SVD between 1998 and 2016 at the Hôpital Broussais (Paris, France) and the Hôpital Européen Georges Pompidou (HEGP, Paris, France). Only patients having undergone a secondary SVR for SVD of ≥1 bioprosthetic valves were selected. Serum was taken within the 2 days before surgery. Clinical and surgical data at the time of bioprosthetic valve implantation and explantation were retrieved from the medical records of the Hôpital Broussais and HEGP. Fifty subjects without heart valve diseases from FARIVE study were used to establish normal range of biomarkers in serum. FARIVE is a French multicenter case-control study carried out between 2003 and 2009 with the aim of studying the interactions of environmental, genetic, and biological risk factors for first VTE and risk of recurrence. Controls were inpatients and outpatients free of history of venous or arterial thrombotic disease. All patients and controls signed the informed consent, and the study was performed in accordance with the Declaration of Helsinki. This study was approved by Paris' regional Ethics Committee (Project n° 2002-034).

Sample Collection

All patients were evaluated before bioprosthetic valve replacement. Trained medical personnel collected antecubital venous blood samples. Twelve mL of blood was collected into gel serum separator tubes and the samples were centrifuged at 15.000 g for 15 min at 20° C. Serum was promptly divided into aliquots and was immediately stored at −80° C. until analyzed.

Protein Quantification

Levels of vascular endothelial growth factor A (VEGF-A, reference DVE00), platelet derived growth factor BB (PDGF-BB, reference DBB00, soluble endoglin (sENG, reference DNDG00), Tumor growth factor beta 1 (TGF-β1, reference DB100B) and thrombospondin-1 (TSP-1, reference DTSP10) in serum samples were quantified using the Human Quantikine kits (enzyme-linked immunosorbent assay, R&D Systems) according to the manufacturers' instructions. Levels of TGF-β1 were measured after samples acidification to detect the active and latent forms, according to the manufacturer's instructions. Soluble endothelial protein C receptor (sEPCR) was quantified using the asserachrom kit (enzyme-linked immunosorbent assay, Diagnostica Stago, Asnières-sur-Seine, France) according to the manufacturer's protocol.

Statistical Analysis

Continuous data were expressed as mean±standard deviation (SD). Categorical data were expressed as frequencies and percentages. In the case of absence of linearity, continuous variables were dichotomized according to the median. Univariate comparisons used the $\chi 2$ test for categorical variables and Student's t test or Mann-Whitney-Wilcoxon test, when appropriate, for continuous variables. Patients were compared according to the bioprosthetic valve calcification status. The inventors performed a focused principal component analysis (FPCA) as an explanatory method for providing clinical and biological patterns associated to bioprosthetic valve calcification. The inventors calculated the p for trend to explore the trend between the proportion of bioprosthesis valve calcification and the increase of biomarkers (sEPCR, VEGF-A, and TSP-1) and patient's age at valve implantation. The inventors have set-up multivariate logistic regression to evaluate the association between bioprosthetic valve calcification status and clinical factors and serum levels of sEPCR. To assess the performance of sEPCR to diagnose the bioprosthetic valve calcification and determine the optimal cut off values, the inventors used the Receiver Operating Characteristic (ROC) method. The diagnostic performance of sEPCR is quantified by calculating the area under the curve (AUC). All analyses were two-sided and a p-value was considered as statistically significant for $p<0.05$. Statistical analysis was performed using Stata 14/SE software (College Station, Tex., US).

Results

Patient Characteristics 119 patients who had undergone bioprosthetic SVR for SVD during the study period were selected. 32 patients were excluded due to blood sampling post-surgery and 13 for incomplete medical record. Study group was composed of 74 patients with SVD who met inclusion criteria. Mean age was 60.3 (±12.9) years and 51/74 patients (68.9%) were men. Patient characteristics are shown in table 2 below. Briefly, 27 (36.5%) patients had overweight, 27 (36.5%) hypertension, 21 (28.4%) dyslipidemia, 21 (28.4%) smoking habits and 4 (5.4%) diabetes. There were no differences in age, sex and cardiovascular risk factors between patients with SVD and the control group. Mean age at implantation was 46.3 (±12.9) years. The redo surgery was redux for 55 (74.3%), tridux for 13 (17.5%) and quadridux for 6 (8.1%) patients.

TSP-1, sCD62E, sEPCR, TGF-131 and sENG levels were 308.70±275.69 pg/mL, 1981.29±1142.93 pg/mL, 12012.20±6435.50 ng/mL, 24.62±12.16 ng/mL, 127.89±59.25 ng/mL, 11763.40±4696.51 pg/mL and

TABLE 2

Baseline characteristics of patients and controls.

| | Patients with SVD | | | | |
|---|---|---|---|---|---|
| | Total | calcification | no calcification | Controls | |
| | | n | | | |
| | 74 | 35 | 39 | 50 | p-value |
| Male sex - n (%) | 51 (68.9) | 25 (71.4) | 26 (66.7) | 30 (60.0) | 0.34** |
| Age (years) - mean (sd) | 60.3 (±12.9) | 58.2 (±11.3) | 62.2 (±14.1) | 60.6 (±13.9) | 0.88** |
| Overweight - n (%) | 27 (36.5) | 13 (37.1) | 14 (35.9) | 19 (38.0) | 0.62** |
| Smoking - n (%) | 21 (28.4) | 11 (31.4) | 10 (25.6) | 24 (48.0) | 0.63** |
| Hypertension - n (%) | 27 (36.5) | 14 (40.0) | 13 (33.3) | 26 (52.0) | 0.57** |
| Diabetes mellitus - n (%) | 4 (5.4) | 2 (5.7) | 2 (5.1) | 11 (22.0) | 0.86** |
| Dyslipidemia - n (%) | 21 (28.4) | 10 (28.6) | 11 (28.2) | 16 (32.0) | 0.70** |
| Chronic kidney disease - n (%) | 4 (5.4) | 1 (2.8) | 3 (7.7) | 0 (0) | |
| Coronary artery disease- n (%) | 1 (1.4) | 0 (0) | 0 (0) | 0 (0) | 0.99** |
| Degenerative bioprosthetic valve position | | | | | |
| Aortic - n (%)* | 57 (77.0) | 29 (82.8) | 28 (71.8) | NA | |
| Mitral - n (%)* | 18 (24.4) | 5 (14.3) | 13 (33.3) | NA | |
| Tricuspid - n (%) | 1 (1.3) | 0 (0) | 1 (2.5) | NA | |
| Pulmonary - n (%)* | 1 (1.3) | 1 (2.8) | 0 (0) | NA | |
| Age at implantation (years)- mean (sd) | 46.3 (±12.9) | 43.3 (±12) | 48.9 (±13.5) | NA | |
| biosprothesis survival (years) - mean (sd) | 13.7 (±5.3) | 14.9 (±4.7) | 13.5 (±5.7) | NA | |
| Redux valve surgery - n (%) | 55 (74.3) | 25 (71.4) | 29 (76.3) | NA | |

There were no differences in age, sex and cardiovascular risk factors between patients with SVD and the control group. Data are means ± SD. SVD for structural valve degeneration;
*Patients may have had more than one type of degenerative bioprosthetic valve.
**Univariate comparisons between total patients with SVD and controls for each variable is not significant (p > 0.05).

Characteristics of Degenerative Bioprosthetic Valves

The total bioprosthetic valves with SVD were localized for 57 (77.0%) in aortic, 18 (24.4%) in mitral, 1 (1.4%), in triscupid and 1 (1.4%) in pulmonary positions. 3 (4.1%) patients had SVD in both aortic and mitral positions and 1 (1.4%) had SVD on both aortic and pulmonary positions. The average bioprosthetic valve survival was 13.7 (±5.3) years. Among the patients with SVD, 35 (47.3%) had surgery because of calcification, 4 (5.4%) because of stenosis, 3 (4.0%) because periprosthetic leakage, 4 (5.4%) because of desinsertion, and 2 (2.7%) because of leaflet tear and one (1.4%) with endocarditis. In patients with bioprosthetic valve calcification, 25 (71.4%) were men with an average age of 58.2 (±11.3) years. In the total cohort, age at implantation was significant lower in the group of patients with calcified bioprosthetic valve (43.3±12.0) compared with patients without (48.9±13.5, p=0.03). Patients underwent a secondary SVR with 18 (23.4%) mechanical and 59 (76.6%) bioprosthetic valves and 3 (3.9%) had Bentall procedures.

Altered Serum Concentration of Endothelial and Angiogenic Biomarkers in SVD Patients Altered serum concentration of endothelial and angiogenic biomarkers levels are summarized in table 3 below. In patients with SVD, mean values for VEGF-A, PDGF-BB, 3.61±1.27 ng/mL respectively. All the biomarkers evaluated were significantly decreased in patients with SVD compared to controls (FIG. 3, p<0.05).

TABLE 3

Biomarker levels of patients with SVD and controls**.

| | Patients with SVD N = 74 | Controls N = 50 | p-value |
|---|---|---|---|
| VEGF-A - pg/mL | 308.70 (±275.69) | 441.22 (±356.75) | 0.024 |
| PDGF-BB - pg/mL | 1981.29 (±1142.93) | 4604.61 (±2311.83) | <0.001 |
| TSP-1 - ng/mL | 12012.20 (±6435.50) | 18923.72 (±10285.61) | <0.001 |
| SCD62E - ng/mL | 24.62 (±12.16) | 47.07 (±23.71) | <0.001 |
| sEPCR - ng/mL | 127.89 (±59.25) | 171.21 (±111.15) | 0.003 |
| TGF-β1 - pg/mL | 11763.40 (±4696.51) | 31774.52 (±9294.19) | <0.001 |
| sENG - ng/mL | 3.61 (±1.27) | 4.34 (±0.95) | <0.001 |
| rT/E | 3521.46 (±1607.70) | 7631.90 (±2991.04) | <0.001 |

SVD for structural valve degeneration; VEGF-A for vascular endothelial growth factor A; PDGF-BB for platelet derived growth factor BB; TSP-1 for thrombospondin-1; sCD62E for soluble E-selectin; sEPCR for Soluble endothelial protein C receptor; sENG for soluble endoglin; TGF-β1 for tumor growth factor beta 1; rT/E for ratio TGF-β1/sENG.
Values are expressed as mean (+/−standard deviation).
**subjects without valve diseases from FARIVE study.

sEPCR Levels are Associated to Bioprosthetic Valve Calcification

No significant differences were found between clinical characteristics and cardiovascular risk factors of patients with or without calcification of the explanted bioprosthetic valve. In the exploratory analysis (FPCA method) correlation between bioprosthetic valve calcification and serum concentrations of the target molecules was analyzed (FIG. 1A). Only sEPCR, VEGF-A and TSP-1 biomarkers as well as the patient's age at valve implantation were on or inside the bold circle (arrow on the graph of FIG. 1) that represents the significant threshold of correlation (FIG. 1A).

Figure 1B:
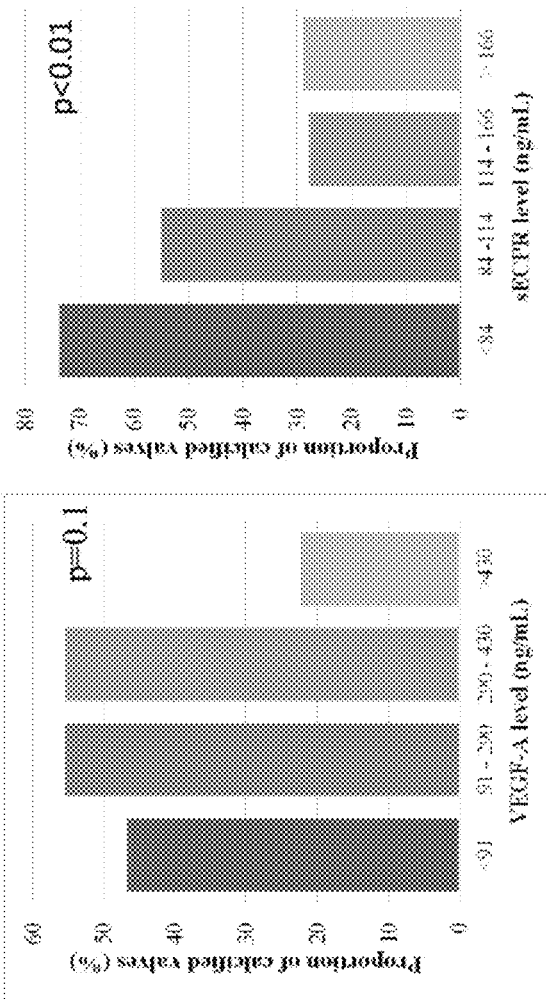
Figure 1E:
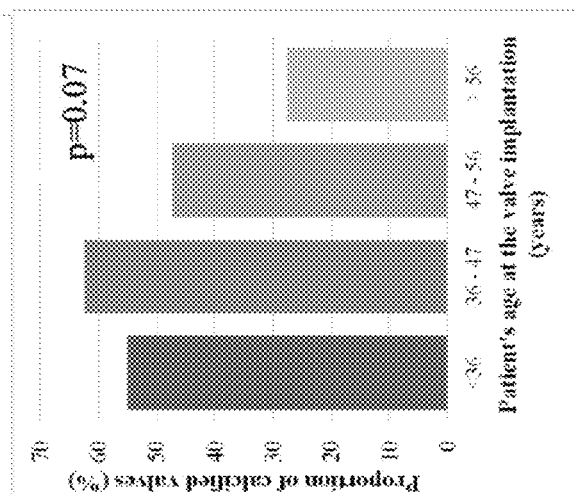
Figure 1D:
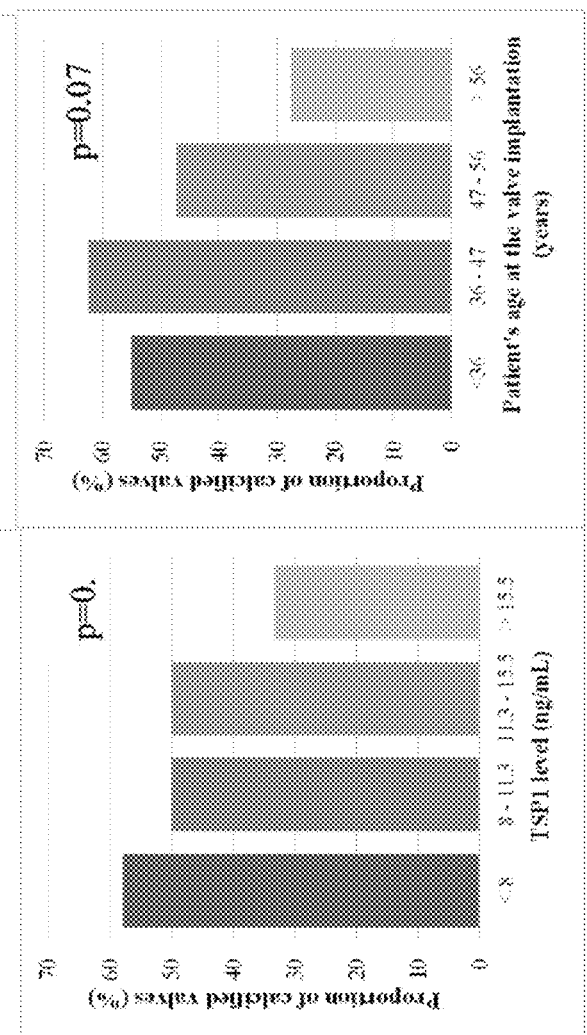

FIGS. 1B, 1C and 1D show the distribution of bioprosthetic valve calcification according to inquartiles of biomarker levels. A significant downward trend for younger age at implantation (0.07) and a significant association of sEPCR levels (p<0.01) was found (FIGS. 1A and 1B). Conversely, lowest levels of VEGF-A and TSP-1 were not significantly associated with bioprosthetic valve calcification (both with a p=0.15). After adjustment for covariates including age, sex and age at valve's implantation, a level of sEPCR lower than 108 ng/mL was significantly associated to risk of calcification of the valve (OR 7.1, 95% CI 2.35-21.47, p<0.001, Table 4 below). The AUC relating decrease in serum sEPCR to risk of bioprothesis valve calcification was 0.736 (FIG. 2). The highest likelihood ratio corresponded to a sEPCR decrease above 108 ng/mL (FIG. 3). This value had a sensitivity of 70.9%, a specificity of 71% and a negative predictive value of 72.9% and positive predictive value of 68.6%.

TABLE 4

Multivariate analysis of clinical factors (gender, age), patient's age at valve implantation and sEPCR level associated with bioprosthesis valve calcification.

|  | aOR (95% CI) | p-value |
|---|---|---|
| Male | 1.78 (0.54-5.8) | 0.336 |
| Age | 1.05 (0.95-1.17) | 0.323 |
| Age at valve's implantation | 0.91 (0.82-1.02) | 0.088 |
| sEPCR < 108.3* ng/mL | 7.1 (2.35-21.47) | <0.001 | aOR for adjusted Odds-ratio; 95% CI: 95% confidence interval.
*dichotomized according to the median.

Conclusion

Inventors show here that a decrease in serum sEPCR may predict valve bioprosthetic valve calcification. These results show a link between endothelial dysfunction, coagulation and calcification of bioprosthetic valve.

II. Lack of EPCR Expression in Valve with Signs of Degeneration and/or Calcification

Sample Collection and IHC Labelling 10 patients who had undergone bioprosthetic SVR for SVD during the study period were selected for histological analysis. All the bioprosthetic SVR specimens were submitted to a standardized dissection protocol of leaflets. Different leaflets were sampled in each case. Between 20 and 25 paraffin blocks were prepared in each case and were stained with hematoxylin and eosin (H&E). Tissue samples were also analyzed with immunohistochemistry. The following markers were used: antiCD45 (Dako), anti-VEcadherin (Invitrogen) and anti-EPCR (Clone 304519, R&D systems). Immunohistochemical studies of paraffin sections were performed following standard procedures, using a three-step avidin-biotin immunoperoxidase method.

Results

FIG. 4 shows representative staining obtained in the study.

Non Degenerative Valve Samples (Control Explanted Bioprosthetic Valves, FIG. 1

The immunohistochemical analysis of CD45 and VE Cadherin revealed that inflammatory cells and endothelial cells are present on non-degenerative valve on top of bioprosthetic materials in agreement with hemocompatibility studies describing hemocompatibility of bovine pericardium. In non-degenerative valve EPCR is detected and found localized is in the intima layer and expressed in inflammatory cells as well as endothelial monolayer which are present at the surface of the bioprosthetic tissue.

Degenerative Valve Samples

The histological analysis revealed in degenerative bioprosthetic valve patients a marked alteration of the EPCR labelling when compared to non-degenerative valves. Indeed, calcified and micro calcified tissue are characterized by the absence of EPCR labelling, even in the inflammatory cells that are still found in the valves. Hence, a complete loss of endothelization and thereby of EPCR expressing endothelial cells is observed in calcified or micro calcified valves, but also a loss of expression of EPCR in inflammatory cells that are still found on these valves.

Conclusion

Inventors showed here that degenerative valves are characterized by a loss of expression of EPCR and a loss of endothelial cells coating, and, as a consequence, EPCR coating.

III. Implanted Valves Expressing EPCR are Less Prone to Degeneration and Calcification

Rat Model Implantation

Subcutaneous implantation in the Wistar rat is a recognized model of calcification, although it does not fully reflect the physiology of valve degeneration because of the absence of characteristic shear stress in the arterial environment (Lila N et al., 2010).

Preparation of in Vitro Disks

The pericardium used is bovine pericardium (Neovasc), preserved in a solution of glutaraldehyde (0.6%). Discs of a 8 mm diameter are cut with a cutaneous biopsy punch, then rinsed in a bath of TBS (Tris Buffer Saline) filtered+SVF 10%. This solution is prepared from TBS 20×, diluted 20 times and then filtered using a 0.20 µl filter, before addition of fetal calf serum (FCS), in a final concentration of 10%. This rinse removes the phosphate from the preservative solution (GTA-PBS) and prevents its precipitation during the formation of the fibrin clot (see below). It also eliminates glutaraldehyde, which is toxic to cells. After this first step, we put on top of the 8 mm diameter disk a solution with Tissue Factor+Phospholipids (PPP Reagent, Thrombinoscope BV) and platelet-poor plasma (PPP) (cryocheck Pooled Normal Plasma)+calcium. To form the fibrin clot, calcium is added to the solution (PPP+PP Reagent), and this final solution is homogenized before being deposited on the pericardial disks arranged in a 24-well plate. Note that this last step is to achieve quickly, before the clot begins to form. The disks are placed in the incubator for 2 hours to obtain the desired fibrin clot on top of the disk.

Endothelial progenitor cells (endothelial colony forming cells, ECFC, Smadja D M et al (2019)) are cultured on both sides of the disk in Eppendorf: 200 000 ECFC per face, 6 h interval between the two faces, culture over 24 h before implantation in rats.

Four type of bioprosthetic tissue were tested: bioprosthetic tissue not covered by fibrin, bioprosthetic tissue covered by fibrin, bioprosthetic tissue covered by fibrin but coated with ECFC, bioprosthetic tissue covered by fibrin but coated with ECFC in which EPCR expression is abolished. ECFC transformation protocol can be found in Smadja et al (2008).

Implantation in Rats

Rats used are Wistar rats, a model of choice for long-term studies because of their longevity. The young rats are delivered with their mother. Female male equity is required. The requested delivery age is 11 days, in order to implant the pups at the predefined age of 12 days. The induction of anesthesia is performed in a hermetic box under 2.5% isoflurane and then masked during implantation, an injection of buprenorphine is performed (buprenorphine 0.05 mg/kg SC) once effective anesthesia. The implantation area is disinfected with dermal Betadine, then the skin is incised with scissors, the subcutaneous plan is taken off, and the disc is inserted as far as possible from the subcutaneous incision point. Four discs are inserted per rat in the dorsal position. The animals are placed on a heating mat and are monitored until they wake up. Once fully awake only, the pups are caged with their mother to avoid possible mutilation if they have not fully awakened and sedated. Implants were collected at day 5, 10, and 14 from implantation. To collect implants, the animals are killed by injection of 2 ml pentobarbital (MED'VET) intraperitoneally after anesthesia with isoflurane (same protocol as for implantation). Following killing, the bovine pericardial disks are explanted with a midline incision and dorsal cutaneous plane. Macroscopic examination of implantation sites is performed. Calcium dosage of pericardial disks is performed by flame atomic absorption spectrophotometer.

Results

Results are presented in table 5 below. When fibrin is put the top of pericardium disk, increased calcification of the tissue is observed. When ECFC are cultivated on top of fibrin, calcification process is abolished, with calcification level comparable to that of non fibrinated tissues. In fibrinated tissues coated with ECFC but not expressing EPCR, calcification of the tissues is observed. So, endothelial coating on pericardium decreases calcification of biomaterials in a EPCR dependent manner.

TABLE 5 calcification quantification of implanted bioprosthetic tissues

| | No fibrin No ECFC | Fibrinated | Fibrinated ECFC coated | Fibrinated ECFC coated (EPCR−) |
|---|---|---|---|---|
| Day 5 | − | + | − | + |
| Day 10 | −/+ | ++ | −/+ | ++ |
| Day 14 | −/+ | ++ | −/+ | ++ |

"−": few calcification,
"−/+": low calcificationm
"+": calcification,
"++": marked calcification Conclusion Inventors showed here that bioprosthetic tissue coated with endothelial cells expressing EPCR are less prone to calcification process. Then coating of bioprosthetic valves with either EPCR or endothelial cell expressing EPCR is a valuable strategy to provide more durable bioprosthetic valves, less prone to degeneration and/or calcification processes once implanted.

Reference to a "Sequence Listing," a Table, or a Computer Program Listing Appendix Submitted as an ASCII Text File The material in the ASCII text file, named "APIC-61742-Sequence-Listing_ST25.txt", created Nov. 6, 2019, file size of 8,192 bytes, is hereby incorporated by reference.

REFERENCE

Chikwe J, Filsoufi F, Carpentier A F. Prosthetic valve selection for middle-aged patients with aortic stenosis. Nat Rev Cardiol. 2010; 7:711-719.

Goldstone A B, Chiu P, Baiocchi M, Lingala B, Patrick W L, Fischbein M P, Woo Y J. Mechanical or Biologic Prostheses for Aortic-Valve and Mitral-Valve Replacement. N Engl J Med. 2017; 377:1847-1857.

Rodriguez-Gabella T, Voisine P, Puri R, Pibarot P, Rodés-Cabau J. Aortic Bioprosthetic Valve Durability: Incidence, Mechanisms, Predictors, and Management of Surgical and Transcatheter Valve Degeneration. J Am Coll Cardiol. 2017; 70:1013-1028.

Shetty R, Pepin A, Charest A, Perron J, Doyle D, Voisine P, Dagenais F, Pibarot P, Mathieu P. Expression of bone-regulatory proteins in human valve allografts. Heart Br Card Soc. 2006; 92:1303-1308.

Noble S, Asgar A, Cartier R, Virmani R, Bonan R. Anatomo-pathological analysis after CoreValve Revalving system implantation. EuroIntervention J Eur Collab Work Group Intent Cardiol Eur Soc Cardiol. 2009; 5:78-85.

Skowasch D, Schrempf S, Wernert N, Steinmetz M, Jabs A, Tuleta I, Welsch U, Preusse C J, Likungu J A, Welz A, Lüderitz B, Bauriedel G. Cells of primarily extra-valvular origin in degenerative aortic valves and bioprostheses. Eur Heart J. 2005; 26:2576-2580.

Smadja D M, Saubaméa B, Susen S, Kindo M, Bruneval P, Van Belle E, Jansen P, Roussel J-C, Latrémouille C, Carpentier A. Bioprosthetic Total Artificial Heart Induces a Profile of Acquired Hemocompatibility With Membranes Recellularization. J Am Coll Cardiol. 2017; 70:404-406.

Pibarot P, Dumesnil J G. Prosthetic Heart Valves: Selection of the Optimal Prosthesis and Long-Term Management. Circulation. 2009; 119:1034-1048.

Rutkovskiy A, Malashicheva A, Sullivan G, Bogdanova M, Kostareva A, Stensløkken K-O, Fiane A, Vaage J. Valve Interstitial Cells: The Key to Understanding the Pathophysiology of Heart Valve Calcification. J Am Heart Assoc. 2017; 6.

Skowasch D, Steinmetz M, Nickenig G, Bauriedel G. Is the degeneration of aortic valve bioprostheses similar to that of native aortic valves? Insights into valvular pathology. Expert Rev Med Devices. 2006; 3:453-462.

Chollet C, Chanseau C, Brouillaud B, Durrieu M C. RGD peptides grafting onto poly(ethylene terephthalate) with well controlled densities. Biomol Eng. 2007 November; 24(5): 477-154 82.

Lila N, McGregor C G, Carpentier S, Rancic J, Byrne G W, Carpentier A. Gal knockout pig pericardium: new source of material for heart valve bioprostheses. J Heart Lung Transplant. 2010 May; 29(5):538-43

Smadja D M, Melero-Martin J M, Eikenboom J, Bowman M, Sabatier F, Randi A M. Standardization of methods to quantify and culture endothelial colony-forming cells derived from peripheral blood: Position paper from the International Society on Thrombosis and Haemostasis SSC. J Thromb Haemost. 2019 July; 17(7):1190-4.

Pan S, Aebersold R, Chen R, Rush J, Goodlett D R, McIntosh M W, Jing Zhang J and Brentnall T A. Mass spectrometry based targeted protein quantification: methods and applications. J Proteome Res. 2009 February; 8(2): 787-797.

Jordan J E, Williams J K, Lee S J, Raghavan D, Atala A, Yoo J J. Bioengineered self-seeding heart valves. J Thorac Cardiovasc Surg. 2012 January; 143(1):201-8.

Dong X, Wei X, Yi W, Gu C, Kang X, Liu Y, Li Q, Yi D. (2009). RGD-modified acellular bovine pericardium as a bioprosthetic scaffold for tissue engineering. J Mater Sci Mater Med, Vol. 20, pp. (2327-2336)

Smadja D M, Bièche I, Susen S, Mauge L, Laurendeau I, d'Audigier C, Grelac F, Emmerich J, Aiach M, Gaussem P. Interleukin 8 is differently expressed and modulated by PAR-1 activation in early and late endothelial progenitor cells J Cell Mol Med. 2009 August; 13(8b): 2534-2546.

Smadja D M, Bieche I, Helley D, Laurendeau I, Simonin G, Muller L, Aiach M, Gaussem P. Increased VEGFR2 expression during human late endothelial progenitor cells expansion enhances in vitro angiogenesis with up-regulation of integrin alpha(6). J Cell Mol Med 2007; 11: 1149-61.

Saposnik B, Lesteven E, Lokajczyk A, Esmon C T, Aiach M, Gandrille S. Alternative mRNA is favored by the A3 haplotype of the EPCR gene PROCR and generates a novel soluble form of EPCR in plasma. *Blood.* 2008; 111(7):3442-3451. doi:10.1182/blood-2007-08-104968.

---

The invention claimed is:

1. A method for diagnosing or monitoring a risk of bioprosthetic valve degeneration, said method comprising the following steps:
   i) selecting a subject that has undergone bioprosthetic surgical valve replacement;
   ii) measuring sEPCR level or amount in a biological sample previously collected from said subject, and
   iii) comparing said level or amount to a reference, wherein diagnosis or monitoring is based on the result of the comparing step.

2. The method for diagnosing or monitoring according to claim 1, wherein measuring sEPCR level or amount according to step ii) comprises contacting said sample with a sEPCR binding partner.

3. A method for diagnosing or monitoring a risk of bioprosthetic valve degeneration in a subject, said method comprising the following steps:
   i) measuring sEPCR level or amount in a biological sample previously collected from said subject, and
   ii) comparing said level or amount to a reference, wherein diagnosis or monitoring is based on the result of the comparing step, and
   wherein said method further comprises a pretreatment step of said sample before step i).

4. The method for diagnosing or monitoring according to claim 3 wherein said pretreatment step comprises a transformation of sEPCR for measuring the level or amount of sEPCR.

5. The method for diagnosing or monitoring according to claim 4 wherein the step ii) comprises contacting the transformed sEPCR with a binding partner capable of selectively interacting with said transformed sEPCR.

6. A method for diagnosing or monitoring a risk of bioprosthetic valve degeneration in a subject, said method comprising the following steps,
   i) measuring sEPCR level or amount in a biological sample previously collected from said subject, and
   ii) comparing said level or amount to a reference, wherein diagnosis or monitoring is based on the result of the comparing step, and wherein when the level of sEPCR is lower than 130 ng/mL, then the subject is diagnosed as suffering or at risk of suffering from bioprosthetic valve degeneration.

7. A method for diagnosing or monitoring a risk of bioprosthetic valve degeneration in a subject, said method comprising the following steps,
   i) measuring sEPCR level or amount in a biological sample previously collected from said subject, and
   ii) comparing said level or amount to a reference wherein diagnosis or monitoring is based on the result of the comparing step, and
   wherein the level of sEPCR is lower than 108 ng/mL, then the subject is diagnosed as suffering or at risk of suffering from bioprosthetic valve degeneration.

8. The method for diagnosing or monitoring according to claim 1, wherein the sample is selected from whole blood, serum or plasma.

9. The method for diagnosing or monitoring according to claim 1 further comprising a step iv) consisting in implementing appropriate health care measures for said subject when the sEPCR level or amount is lower than the reference level or amount defined in step iii).

10. The method of diagnosing or monitoring according to claim 9, wherein the implemented healthcare measure is selected from administering to said subject at least one anticoagulant medication, at least one preventive treatment or measure of heart failure or atrial fibrillation, or performing on said subject an echocardiography, or a combination thereof.

11. A bioprosthetic tissue to be implanted in the body of a subject coated with EPCR protein, sEPCR, extracellular part of EPCR, or a fragment thereof.

12. The bioprosthetic tissue according to claim 11, wherein said bioprosthetic tissue comprises a chemically grafted sEPCR, a chemically grafted extracellular part of EPCR or a chemically grafted fragment thereof tissue.

13. The bioprosthetic tissue according to claim 11, wherein the tissue is colonized with cells expressing EPCR.

14. The bioprosthetic tissue according to claim 11, wherein the tissue is made of bovine, calf, equine, or porcine pericardium, or of porcine aortic valve.

15. A bioprosthetic valve to be implanted in a subject comprising a tissue according to claim 14.

16. A device adapted for carrying out the method of diagnosing or monitoring according to any of claims 1 to 8 comprising:
   an analyzing unit adapted for measuring the amount or level of sEPCR in a sample of a subject; and
   an evaluation unit comprising a stored reference and a data processor having implemented an algorithm for comparing the amount of sEPCR measured by the analyzing unit with at least one stored reference.

17. A method of treating slowing or stopping bioprosthetic valve degeneration and/or calcification in a subject suffering or at risk of suffering from valve degeneration and/or calcification, comprising administering to the subject at least one anticoagulant medication, selected from:
   a vitamin K antagonist,
   an heparinoid,
   an antiplatelets agents,
   a thrombin inhibitor,
   an inhibitor of factor Xa,
   other antiplatelet agents, or
   a combination thereof.

18. A method of treating valvopathy comprising using a bioprosthetic valve according to claim 15.

19. The method of claim 6, wherein when the level of sEPCR is lower than 110 ng/mL, then the subject is diagnosed as suffering or at risk of suffering from bioprosthetic valve degeneration.

20. The method of claim 17, wherein the anticoagulant medication is acetylsalicylic acid.

* * * * *

SEQUENCE LISTING

```
<160> NUMBER OF SEQ ID NOS: 2

<210> SEQ ID NO 1
<211> LENGTH: 238
<212> TYPE: PRT
<213> ORGANISM: Homo sapiens

<400> SEQUENCE: 1

Met Leu Thr Thr Leu Leu Pro Ile Leu Leu Leu Ser Gly Trp Ala Phe
1               5                   10                  15

Cys Ser Gln Asp Ala Ser Asp Gly Leu Gln Arg Leu His Met Leu Gln
            20                  25                  30

Ile Ser Tyr Phe Arg Asp Pro Tyr His Val Trp Tyr Gln Gly Asn Ala
        35                  40                  45

Ser Leu Gly Gly His Leu Thr His Val Leu Glu Gly Pro Asp Thr Asn
    50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
            100                 105                 110

Arg Cys Phe Leu Gly Cys Glu Leu Pro Pro Glu Gly Ser Arg Ala His
        115                 120                 125

Val Phe Phe Glu Val Ala Val Asn Gly Ser Ser Phe Val Ser Phe Arg
    130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
```

```
                195                 200                 205
Thr Ser Leu Val Leu Gly Val Leu Val Gly Gly Phe Ile Ala Gly
        210                 215                 220
Val Ala Val Gly Ile Phe Leu Cys Thr Gly Gly Arg Arg Cys
225                 230                 235

<210> SEQ ID NO 2
<211> LENGTH: 192
<212> TYPE: PRT
<213> ORGANISM: Homo sapiens

<400> SEQUENCE: 2

Cys Ser Gln Asp Ala Ser Asp Gly Leu Gln Arg Leu His Met Leu Gln
1               5                   10                  15

Ile Ser Tyr Phe Arg Asp Pro Tyr His Val Trp Tyr Gln Gly Asn Ala
            20                  25                  30

Ser Leu Gly Gly His Leu Thr His Val Leu Glu Gly Pro Asp Thr Asn
        35                  40                  45

Thr Thr Ile Ile Gln Leu Gln Pro Leu Gln Glu Pro Glu Ser Trp Ala
    50                  55                  60

Arg Thr Gln Ser Gly Leu Gln Ser Tyr Leu Leu Gln Phe His Gly Leu
65                  70                  75                  80

Val Arg Leu Val His Gln Glu Arg Thr Leu Ala Phe Pro Leu Thr Ile
                85                  90                  95

Arg Cys Phe Leu Gly Cys Glu Leu Pro Pro Glu Gly Ser Arg Ala His
            100                 105                 110

Val Phe Phe Glu Val Ala Val Asn Gly Ser Ser Phe Val Ser Phe Arg
        115                 120                 125

Pro Glu Arg Ala Leu Trp Gln Ala Asp Thr Gln Val Thr Ser Gly Val
    130                 135                 140

Val Thr Phe Thr Leu Gln Gln Leu Asn Ala Tyr Asn Arg Thr Arg Tyr
145                 150                 155                 160

Glu Leu Arg Glu Phe Leu Glu Asp Thr Cys Val Gln Tyr Val Gln Lys
                165                 170                 175

His Ile Ser Ala Glu Asn Thr Lys Gly Ser Gln Thr Ser Arg Ser Tyr
            180                 185                 190
```